United States Patent
Goletz et al.

(10) Patent No.: US 9,487,567 B2
(45) Date of Patent: Nov. 8, 2016

(54) METHOD FOR THE PRODUCTION OF AN IMMUNOSTIMULATING MUCIN (MUC1)

(71) Applicant: Glycotope GmbH, Berlin (DE)

(72) Inventors: Steffen Goletz, Glienicke-Nordbahn (DE); Uwe Karsten, Panketal (DE)

(73) Assignee: GLYCOTOPE GMBH, Berlin (DE)

( * ) Notice: Subject to any disclaimer, the term of this patent is extended or adjusted under 35 U.S.C. 154(b) by 139 days.

(21) Appl. No.: 14/148,161

(22) Filed: Jan. 6, 2014

(65) Prior Publication Data

US 2015/0010495 A1 Jan. 8, 2015

Related U.S. Application Data

(60) Division of application No. 12/818,839, filed on Jun. 18, 2010, now Pat. No. 8,642,276, which is a continuation of application No. 10/522,087, filed as application No. PCT/EP03/08014 on Jul. 22, 2003, now abandoned.

(30) Foreign Application Priority Data

Jul. 22, 2002 (EP) .................................. 02016440

(51) Int. Cl.
| | |
|---|---|
| *A61K 39/00* | (2006.01) |
| *C07K 17/00* | (2006.01) |
| *C07K 14/00* | (2006.01) |
| *C07K 1/00* | (2006.01) |
| *C07K 14/47* | (2006.01) |
| *C07K 16/30* | (2006.01) |
| *C07K 16/44* | (2006.01) |
| *A61K 38/17* | (2006.01) |
| *A61K 45/06* | (2006.01) |

(52) U.S. Cl.
CPC ....... *C07K 14/4727* (2013.01); *A61K 38/1735* (2013.01); *A61K 39/0005* (2013.01); *A61K 45/06* (2013.01); *C07K 16/3092* (2013.01); *C07K 16/44* (2013.01); *A61K 2039/505* (2013.01)

(58) Field of Classification Search
None
See application file for complete search history.

(56) References Cited

U.S. PATENT DOCUMENTS

| 4,939,240 | A | 7/1990 | Chu et al. |
| 5,688,657 | A | 11/1997 | Tsang et al. |
| 2009/0054622 | A1 | 2/2009 | Hanisch et al. |

FOREIGN PATENT DOCUMENTS

CA 2 375 033 A1 12/2000

OTHER PUBLICATIONS

Dahiya et al., Cancer Res., 1993, 53, 1437-1443.*
Gimmi et al., Breast-cancer associated antigen DF3/MUC1, induces apoptosis of activated human T cells, *Nature Medicine* 2(12):1367-1370, 1996.
Norum et al., "Carcinoma-Associated MUC1 Detected by Immunoradiometric Assays," *Tumor Biology* 19(Suppl 1):134-146, 1998.
Paul, William, *Fundamental Immunology*, 3rd edition, Raven Press, New York, 1993.
Price et al., "Summary Report on the ISOBM TD-4 Workshop: Analysis of 56 Monoclonal Antibodies against the MUC1 Mucin," *Tumor Biology* 19(Suppl 1): 1-20, 1998, p. 242.
Ryuko et al., "Characterization of a New MUC1 Monoclonal Antibody (VU-2-G7) Directed to the Glycosylated PDTR Sequence of MUC1," *Tumor Biology* 21(4):197-210, 2000.
Snijdewint et al., "Cellular and humoral immune responses to MUC1 mucin and tandem-repeat peptides in ovarian cancer patients and controls," *Cancer Immunology Immunotherapy* 48(1):47-55, 1999.

* cited by examiner

*Primary Examiner* — Hong Sang
(74) *Attorney, Agent, or Firm* — Seed Intellectual Property Law Group PLLC

(57) ABSTRACT

The present invention relates to a method for producing or identifying a MUC1 molecule which is able to generate an immune response in humans. The invention also relates to a method for producing or identifying a cell, cell lines or cell lysates containing a MUC1 molecule that is able to generate an immune response in humans. The invention further relates to methods for producing medicaments and diagnostic agents. Also disclosed is the use of the MUC1 molecules, cells or cell lysates obtained by means of the methods according to the invention for producing a medicament used for treating or preventing tumors. Further disclosed is a purified MUC1 molecule that can be obtained by means of the methods according to the invention and has an immunostimulating effect on humans. The invention additionally relates to the use of a MUC1 antibody for the production of a medicament used for treating or preventing tumors.

7 Claims, 16 Drawing Sheets

Binding of the mab A76-A/C7 (type GD-1) to a MUC1
30-mer depending on the glycosylation to the PDTR motif Binding pattern of mab against MUC1 of the epitope with GalNAc:
VU-3C6 (type GD-2), VU-4H5 (type iGD), HMFG-1 (type GI)

Binding of the mab A76-A/C7 to glycosylated MUC1 peptides of different length (1-5 tandem repeats) (glycosylated with Tn to PDTR motif)

Binding of the mab Mc5 to glycosylated MUC1 peptides of different length
(1-5 tandem repeats)
(glycosylated with Tn to PDTR motif)

Binding of the mab VU-4H5 to glycosylated MUC1 peptides of different length (1-5 tandem repeats) (glycosylated with Tn to PDTR motif)

1) ZR-75-1 cells before accumulation with A76-A/C7 and cloning

2) ZR-75-1 cells after accumulation with A76-A/C7 and cloning (ZR-75-1-sub)

Figure 5C (1)

A. Expression vector

B. Sequenz of the human muc1 cDNA, which were cloned into the expression vector. The primers which were used for the amplification of the cDNA from ZR-75-1 cDNA are marked in green.

```
        GAATTCCCTG GCTGCTTGAA TCTGTTCTGC CCCCTCCCCA CCCATTTCAG
  1     ---------- ---------- ---------- ---------- ----------
        CTTAAGGGAC CGACGAACTT AGACAAGACG GGGGAGGGGT GGGTAAAGTG
              +10        +20        +30        +40
        AGCCACCATGTACACGGGCA CCCAGTCTCC TTTCTTCCTG CTGCTGCTCC
 51     ----------** ********** ********** ********** **********
        GTGGTGGTAC TGTGCCCGT GGGTCAGAGG AAAGAAGGAC GACGACGAGG
              +10        +20        +30        +40
        TCACAGTGCT TACAGTTGTT ACAGGTTCTG GTCATGCAAG CTCTACCCCA
101     ********** ********** ********** ********** **********
        AGTGTCACGA ATGTCAACAA TGTCCAAGAC CAGTACGTTC GAGATGGGGT
              +10        +20        +30        +40
        GGTGGAGAAA AGGAGACTTC GGCTACCCAG AGAAGTTCAG TGCCCAGCTC
151     ********** ********** ********** ********** **********
        CCACCTCTTT TCCTCTGAAG CCGATGGGTC TCTTCAAGTC ACGGGTCGAG
              +10        +20        +30        +40
        TACTGAGAAG AATGCTGTGA GTATGACCAG CAGCGTACTC TCCAGCCACA
201     ********** ********** ********** ********** **********
        ATGACTCTTC TTACGACACT CATACTGGTC GTCGCATGAG AGGTCGGTGT
              +10        +20        +30        +40
        GCCCCGGTTC AGGCTCCTCC ACCACTCAGG GACAGGATGT CACTCTGGCC
251     ********** ********** ********** ********** **********
        CGGGGCCAAG TCCGAGGAGG TGGTGAGTCC CTGTCCTACA GTGAGACCGG
              +10        +20        +30        +40
        CCGGCCACGG AACCAGCTTC AGGTTCAGCT GCCACCTGGG GACAGGATGT
301     ********** ********** ********** ********** **********
        GGCCGGTGCC TTGGTCGAAG TCCAAGTCGA CGGTGGACCC CTGTCCTACA
              +10        +20        +30        +40
        CACCTCGGTC CCAGTCACCA GGCCAGCCCT GGGCTCCACC ACCCCGCCAG
351     ********** ********** ********** ********** **********
        GTGGAGCCAG GGTCAGTGGT CCGGTCGGGA CCCGAGGTGG TGGGGCGGTC
              +10        +20        +30        +40
        CCCACGATGT CACCTCAGCC CCGGACAACA AGCCAGCCCC GGGCTCCACC
401     ********** ********** ********** ********** **********
        GGGTGCTACA GTGGAGTCGG GGCCTGTTGT TCGGTCGGGG CCCGAGGTGG
              +10        +20        +30        +40
        GCCCCCCCAG CCCACGGTGT CACCTCGGCC CCGGACACCA GGCCGCCCCC
451     ********** ********** ********** ********** **********
        CGGGGGGGTC GGGTGCCACA GTGGAGCCGG GGCCTGTGGT CCGGCGGGGG
              +10        +20        +30        +40
        GGGCTCCACC GCCCCCCCAG CCCACGGTGT CACCTCGGCC CCGGACACCA
501     ********** ********** ********** ********** **********
        CCCGAGGTGG CGGGGGGGTC GGGTGCCACA GTGGAGCCGG GGCCTGTGGT
              +10        +20        +30        +40
        GGCCGCCCCC GGGCTCCACC GCGCCCGCAG CCCACGGTGT CACCTCGGCC
551     ********** ********** ********** ********** **********
        CCGGCGGGGG CCCGAGGTGG CGCGGGCGTC GGGTGCCACA GTGGAGCCGG
```

Figure 5C (2)

```
             +10        +20        +30        +40
      CCGGACACCA GGCCGGCCCC GGGCTCCACC GCCCCCCCAG CCCATGGTGT
 601  ********** ********** ********** ********** **********
      GGCCTGTGGT CCGGCCGGGG CCCGAGGTGG CGGGGGGGTC GGGTACCACA
             +10        +20        +30        +40
      CACCTCGGCC CCGGACAACA GGCCCGCCTT GGCGTCCACC GCCCCTCCAG
 651  ********** ********** ********** ********** **********
      GTGGAGCCGG GGCCTGTTGT CCGGGCGGAA CCGCAGGTGG CGGGGAGGTC
             +10        +20        +30        +40
      TCCACAATGT CACCTCGGCC TCAGGCTCTG CATCAGGCTC AGCTTCTACT
 701  ********** ********** ********** ********** **********
      AGGTGTTACA GTGGAGCCGG AGTCCGAGAC GTAGTCCGAG TCGAAGATGA
             +10        +20        +30        +40
      CTGGTGCACA ACGGCACCTC TGCCAGGGCT ACCACAACCC CAGCCAGCAA
 751  ********** ********** ********** ********** **********
      GACCACGTGT TGCCGTGGAG ACGGTCCCGA TGGTGTTGGG GTCGGTCGTT
             +10        +20        +30        +40
      GAGCACTCCA TTCTCAATTC CCAGCCACCA CTCTGATACT CCTACCACCC
 801  ********** ********** ********** ********** **********
      CTCGTGAGGT AAGAGTTAAG GGTCGGTGGT GAGACTATGA GGATGGTGGG
             +10        +20        +30        +40
      TTGCCAGCCA TAGCACCAAG ACTGATGCCA GTAGCACTCA CCATAGCACG
 851  ********** ********** ********** ********** **********
      AACGGTCGGT ATCGTGGTTC TGACTACGGT CATCGTGAGT GGTATCGTGC
             +10        +20        +30        +40
      GTACCTCCTC TCACCTCCTC CAATCACAGC ACTTCTCCCC AGTTGTCTAC
 901  ********** ********** ********** ********** **********
      CATGGAGGAG AGTGGAGGAG GTTAGTGTCG TGAAGAGGGG TCAACAGATG
             +10        +20        +30        +40
      TGGGGTCTCT TTCTTTTTCC TGTCTTTTCA CATTTCAAAC CTCCAGTTTA
 951  ********** ********** ********** ********** **********
      ACCCCAGAGA AAGAAAAAGG ACAGAAAAGT GTAAAGTTTG GAGGTCAAAT
             +10        +20        +30        +40
      ATTCCTCTCT GGAAGATCCC AGCACCGACT ACTACCAAGA GCTGCAGAGA
1001  ********** ********** ********** ********** **********
      TAAGGAGAGA CCTTCTAGGG TCGTGGCTGA TGATGGTTCT CGACGTCTCT
             +10        +20        +30        +40
      GACATTTCTG AAATGTTTTT GCAGATTTAT AAACAAGGGG GTTTTCTGGG
1051  ********** ********** ********** ********** **********
      CTGTAAAGAC TTTACAAAAA CGTCTAAATA TTTGTTCCCC CAAAAGACCC
             +10        +20        +30        +40
      CCTCTCCAAT ATTAAGTTCA GGCCAGGATC TGTGGTGGTA CAATTGACTC
1101  ********** ********** ********** ********** **********
      GGAGAGGTTA TAATTCAAGT CCGGTCCTAG ACACCACCAT GTTAACTGAG
             +10        +20        +30        +40
      TGGCCTTCCG AGAAGGTACC ATCAATGTCC ACGACGTGGA GACACAGTTC
1151  ********** ********** ********** ********** **********
      ACCGGAAGGC TCTTCCATGG TAGTTACAGG TGCTGCACCT CTGTGTCAAG
             +10        +20        +30        +40
      AATCAGTATA AAACGGAAGC AGCCTCTCGA TATAACCTGA CGATCTCAGA
1201  ********** ********** ********** ********** **********
      TTAGTCATAT TTTGCCTTCG TCGAGAGCT ATATTGGACT GCTAGAGTCT
             +10        +20        +30        +40
      CGTCAGCGTG AGTGATGTGC CATTTCCTTT CTCTGCCCAG TCTGGGGCTG
1251  ********** ********** ********** ********** **********
      GCAGTCGCAC TCACTACACG GTAAGGAAA GAGACGGGTC AGACCCCGAC
```

Figure 5C (3)

```
                +10        +20        +30        +40
     GGGTGCCAGG CTGGGGCATC GCGCTGCTGG TGCTGGTCTG TGTTCTGGTT
1301********** ********** ********** ********** **********
     CCCACGGTCC GACCCCGTAG CGCGACGACC ACGACCAGAC ACAAGACCAA
                +10        +20        +30        +40
     GCGCTGGCCA TTGTCTATCT CATTGCCTTG GCTGTCTGTC AGTGCCGCCG
1351********** ********** ********** ********** **********
     CGCGACCGGT AACAGATAGA GTAACGGAAC CGACAGACAG TCACGGCGGC
                +10        +20        +30        +40
     AAAGAACTAC GGGCAGCTGG ACATCTTTCC AGCCCGGGAT ACCTACCATC
1401********** ********** ********** ********** **********
     TTTCTTGATG CCCGTCGACC TGTAGAAAGG TCGGGCCCTA TGGATGGTAG
                +10        +20        +30        +40
     CTATGAGCGA GTACCCCACC TACCACACCC ATGGGCGCTA TGTGCCCCCT
1451********** ********** ********** ********** **********
     GATACTCGCT CATGGGGTGG ATGGTGTGGG TACCCGCGAT ACACGGGGGA
                +10        +20        +30        +40
     AGCAGTACCG ATCGTAGCCC CTATGAGAAG GTTTCTGCAG GTAATGGTGG
1501********** ********** ********** ********** **********
     TCGTCATGGC TAGCATCGGG GATACTCTTC CAAAGACGTC CATTACCACC
                +10        +20        +30        +40
     CAGCAGCCTC TCTTACACAA ACCCAGCAGT GGCAGCCACT TCTGCCAACT
1551********** ********** ********** ********** **********
     GTCGTCGGAG AGAATGTGTT TGGGTCGTCA CCGTCGGTGA AGACGGTTGA
                +10        +20        +30        +40
     TGTAGGGGCA CGTCGCCCTC TGAGCTGAGT GGCCAGCCAG TGCCATTCCA
1601*****----- ---------- ---------- ---------- ----------
     ACATCCCCGT GGAGGGGAGGACTCCAGTGAGCGGTCGGTC ACGGTAAGGT
                +10        +20        +30        +40
     CTCCACTCAG GGCTCTCTGG GCCAGTCCTC CTGGGAGCCC CCACCACAAC
1651---------- ---------- ---------- ---------- ----------
     GAGGTGAGTC CCGAGAGACC CGGTCAGGAG GACCCTCGGG GGTGGTGTTG
                +10        +20        +30        +40
     ACTTCCCAGG CATGGAATTC C
1701---------- ---------- -
     TGAAGGGTCC GTACCTTAAG G
```

Figure 5D (1)

A. Rec site vector

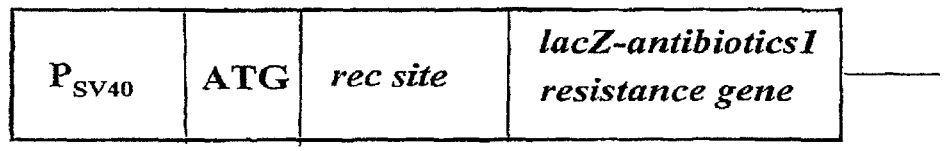

Features of the stably transfected host cells:

- Integration of the recombination site in connection with the lacZ antibiotic1 resistance fusion gene
- Resistance against the antibiotic1, expression of the lacZ gene (β-galactosidase activity)
- The transfectants differ with respect to the strength of the expression of the fusion gene (chromosomal positioning effect) depending on the integration site of the recombination site and of the fusion gene in the chromosome. Detection by ß-galactosidase activities differing in strength.

Figure 5D (2)
A. Integration of the muc1 cDNA via the rec site into the ZR-75-1 genome
Recombinase
Expression vector
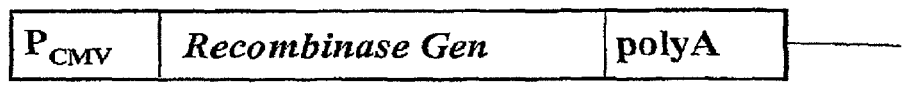
+
Muc1 expression vector with recombination site (rec site)
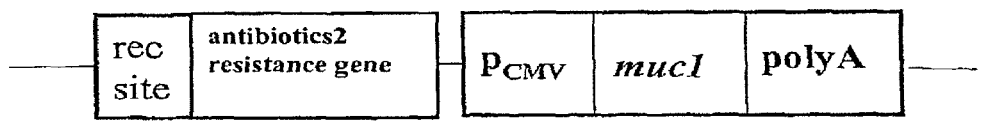
↓ Product of the side-specific recombination

Figure 5D (3)
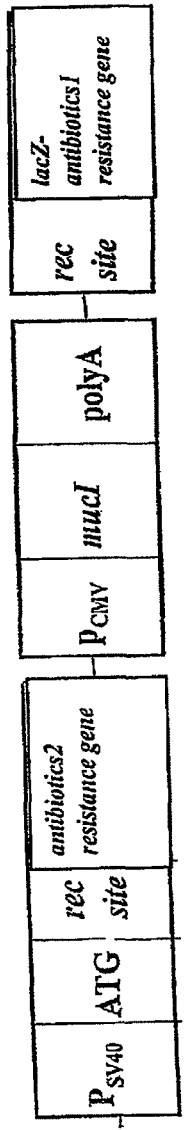
Features of the stably transfected host cells:
- Resistance against antibiotic 2
- Sensitivity to antibiotic 1, ß-galactosidase inactive
- High expression of the recombinant muc1 gene due to the strong promotor and the chromosomal positioning effect BSM - bovine submaxillary mucin 1
MUC1 - Mucin 1 from cell supernatants

METHOD FOR THE PRODUCTION OF AN IMMUNOSTIMULATING MUCIN (MUC1)

CROSS REFERENCE TO RELATED APPLICATIONS

This application is a divisional of U.S. patent application Ser. No. 12/818,839, filed Jun. 18, 2010, now U.S. Pat. No. 8,641,276, which is a continuation of U.S. patent application Ser. No. 10/522,087, filed Jul. 26, 2005 now abandoned, which is a 371 national phase entry of PCT/EP03/08014, filed Jul. 22, 2003, which claims priority to European Patent Application No. EP 02016440.6, filed Jul. 22, 2002, all of which are incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 400086_402D1_SEQUENCE_LISTING.txt. The text file is 8.75 KB, was created on Dec. 26, 2013, and is being submitted electronically via EFS-Web.

The present invention relates to a method for producing or identifying a MUC1 molecule that is able to generate an immune response in humans. The invention also relates to a method for producing or identifying a cell, cell lines, or cell lysates comprising a MUC1 molecule that is able to generate an immune response in humans. The invention further relates to methods for producing medicaments and diagnostic agents. A further object of the present invention is the use of the MUC1 molecules, cells or cell lysates obtainable by means of the methods of the present invention for producing a medicament used for the treatment or prevention of tumours. The invention also relates to a purified MUC1 molecule that can be obtained by means of the methods of the present invention and has an immunostimulating effect on humans. The invention additionally relates to the use of an MUC1 antibody for the production of a medicament used for the treatment or prevention of tumours.

In the past, the human mucin MUC1 was inter alia also called polymorphic epithelial mucin (PEM). At the moment it is the only mucin of which it is known that it is a transmembrane glycoprotein. The polypeptide of the MUC1 consists extracellulary mainly of repetitive units, the so-called tandem repeats, their number in the human population being polymorph for genetic reasons. In agreement with the general characteristic of the mucins, MUC1 also carries a large number of carbohydrate chains joined by 0-glycosidic bond. Each tandem repeat consists of 20 conserved amino acids (NH2-HGVTSAPDTRPAPGSTAPPA-COOH) (SEQ ID NO: 2) with 5 potential O-glycosylation sites (two serines and three threonines). Until recently the general state of knowledge was that the potential glyocsylation site in the PDTR (SEQ ID NO:3) sequence is non-glycosylated (e.g., Finn O J, Jerome K R, Henderson R A, Pecher G, Domenech N, Magarian-Blander J, Barratt-Boyes S M. MUC-1 epithelial tumour mucin-based immunity and cancer vaccines. Imm Revs 145:61-89 (1995), p. 67).

One of the reasons given for this was that after immunization of mice with MUC1 from tumour or non-tumour sources almost exclusively antibodies were generated which are directed against the PDTR (SEQ ID NO:3) region, which therefore is also called immunodominant region. A further reason was that at this time in-vitro glycocsylation attempts were not successful in inducing glycosylation in the PDTR (SEQ ID NO:3) region. Recently, however, it was shown in particular by mass spectrometric analysis of MUC1 from human milk (non-tumour source) that the threonine of the PDTR (SEQ ID NO:3) region of some tandem repeats can be in glycosylated form although others are present in an unglycosylated form. Furthermore, the analysis of a group of MUC1 specific antibodies has shown that a glycosylation in the PDTR (SEQ ID NO:3) region enhances or even first makes possible the binding of individual antibodies Ab to short MUC1 peptides vis-à-vis the unglycosylated peptide, whereas others bind to this site completely independently of glycosylation.

MUC1 per se is an established tumour marker. The following known properties characterize MUC1 as a tumour marker: In the normal epithelium, especially in the epithelium of glands, MUC1 is expressed exclusively polar on the apical membrane of the cells. However, this strict apical localization is lost during carcinogenesis, and it comes to an apolar expression over the whole cell surface, whereby the MUC1 becomes accessible to the immune system. It is a further characteristic of MUC1 that its expression is increased during carcinogenesis. As third known tumour property, the glycosylation of MUC1 changes during carcinogenesis resulting in an aberrant glycosylation. This results on the one hand in the expression of de novo carbohydrate antigens and on the other hand in the partial exposure of peptide epitopes (Karsten, Cancer Research 58, 2541-2549, 1998; Price, Tumor Biol. Suppl1: 1-5, 1998). As described in the prior art, MUC1 is a molecule known per se which is well-established as a tumour marker. However, MUC1 is not a strictly structurally defined molecule but a heterogeneous mixture of molecules. The heterogeneity is caused by various properties of MUC1:

a. MUC1 is genetically polymorph in the human population as regards the number of tandem repeats.
b. Glycosylation and expression vary in different tissues and at different differentiation stages.
c. MUC1 preparations from tissue or cell lines show a high degree of heterogeneity of carbohydrate structures and thus of MUC1 molecules.
d. MUC1 preparations from tissue or cell lines show that within one MUC1 molecule the tandem repeats are heterogeneously glycosylated, this applies to the sugar chains as well as to the glycosylation sites.
e. The techniques available at present do not allow the correlation of a carbohydrate chain to a specific tandem repeat or to a specific glycosylation site of MUC1 from native material.
f. So far glycosylation has not been completely described for any MUC1.

The chemical structure of a natural MUC1 molecule is in no case completely known. To the contrary, the glycosylation is only known in few cases and there only partially. This shows that the conventional native MUC1 is no defined structure but a large heterogeneous group of molecules.

In addition, in case of cancer by changes in the glycosylation apparatus changes occur in the MUC1 glycosylation which introduce a further complexity into the heterogeneity. This changed glycosylation is again strongly heterogeneous in relation to the type of tumour, within one tumour type, with regard to carbohydrate chains, and to the distribution of the carbohydrate chains.

It has been described that tumour-associated MUC1 acts immunosuppressive on T-cell proliferation (Agrawal et al., Nat. Med., 1998, October 4(10):1093). It has been further described that this relates especially to longer MUC1 molecules having more than 60 amino acids, which were obtained from tumour cells (WO 99/23114). A corresponding immunosuppression is particularly disadvantageous or prevents the use of corresponding tumour-associated MUC1 molecules expressed from cells. In particular it has been described that MUC1 obtained by means of the antibody B27.29 suppresses the immune system (US20020044943, WO 9810783). For a suitable and effective tumour therapy or prophylaxis on the basis of the tumour marker MUC1 it is necessary to find a way to produce MUC1 molecules which do not suppress the immune system at all or only to a limited extent, and which, preferably, even act as stimulants to the immune system. An established tumour therapy or prophylaxis on the basis of the tumour marker MUC1 is not known.

The technical problem underlying the present invention is thus to provide measures for therapy and/or prophylaxis of tumours associated with the tumour marker MUC-1.

This technical problem is solved by the embodiments described in the claims.

The present invention thus relates to a method for producing an MUC1 molecule which is able to generate an immune response in humans, comprising:
(a) contacting a mixture of MUC1 molecules with an antibody having the following properties:
  i) binding to the immunodominant region of the MUC1 tandem repeat; and
  ii) the binding to an MUC1 fragment having a length of between 9 and 40 amino acids and containing sequences of the MUC1 tandem repeat and the immunodominant region is made possible or enhanced by glycosylation of the threonine of a PDTR (SEQ ID NO:3) sequence; and
  iii) the binding of unglycosylated MUC1 tandem repeats is enhanced if the unglycosylated MUC1 tandem repeats exist in series; and
  iv) the binding to multiple glycosylated MUC1 tandem repeats carrying glycosylations at the threonines of several PDTR (SEQ ID NO:3) sequences of the immunodominant region is enhanced vis-à-vis the short MUC1 fragments of ii) in view of an additive effect of length and the PDTR (SEQ ID NO:3) glycosylation;
  for a period of time that is sufficient and under conditions that are suitable to form an immune complex;
(b) isolation of the immune complex; and
(c) providing an MUC1 molecule from the immune complex.

In addition to the previously explicitly mentioned steps the term "preparation" also includes additional steps, such as pretreatment of the starting material or further treatment of the final product. Pretreatment procedures will be described in more detail in the following, further treatment procedures comprise e.g. the final formulation of the prepared MUC1 molecule in suitable dosage forms. The kind of dosage form, e.g. tablet, solution or lyophilisate, depends on the intended use. The person skilled in the art knows which dosage form is suitable for which application. Depending on the dosage form used the MUC1 molecule produced by the method of the invention may be present together with excipients, carrier substances or further active agents. Here, excipients are preferably adjuvants, further active agents are preferably immunostimulating molecules, such as interleukins. The MUC1 molecule produced by a method according to the present invention may also be chemically modified in further treatment steps. Here, the MUC1 molecule is preferably combined with one or more further molecules in a suitable manner, i.e. by chemical or physical interaction. Preferably serving as further molecules within the meaning of the invention are other proteins or peptides which are fused with the MUC1 molecule prepared according to the method of the invention, in this case the MUC1 molecule is present as fusion protein. Further molecules within the framework of the inventive method are in particular substances having a therapeutic or diagnostic activity, such as radioisotopes or toxins. Further molecules to be used in connection with the invention are such substances which are suitable to serve as carrier materials or which may serve as components to couple the MUC1 molecules with carrier substances. Such carrier materials or coupling components are known from the prior art.

The term "MUC1 molecule which is able to generate an immune response in humans" comprises MUC1 molecules or fragments thereof which belong to a species of MUC1 glycoproteins which alone or in combination with suitable adjuvants and/or immunostimulating molecules cause an immune response to MUC1-positive tumour cells. An immune response within the meaning of the present invention is the triggering of a humoral immune response and/or cellular immune response. A humoral immune response in the sense of the present invention means the inducing of antibodies by MUC1 molecules produced according to the method of the invention. A cellular immune response means the inducing of immune cells, e.g., CD4-positive and/or CD8-positive cells, by the MUC1 molecules produced according to the method of the present invention, which directly or indirectly fight MUC1-positive tumour cells. The MUC1 molecules are characterized by the fact that they have no or only a weak immunosuppressive effect on T-cells. Preferably used are MUC1 molecules which stimulate T-cells, i.e. these molecules have a stimulating effect within the meaning of the present invention. The MUC1 molecules are preferably tumour-associated. The immunostimulating properties of MUC1 molecules and induced immune responses can be shown in-vitro and in-vivo by at least one of the methods described in the Examples or other methods known to the skilled person, such as ELISA, ADCC- and CDC-assays, T cell stimulation assays and NOD-SCID mouse models. The skilled person is therefore readily able to determine whether certain MUC1 molecules belong to the same species with respect to their immunostimulating properties. Preferably the members of this species share in one or more tandem repeat(s) chemical properties which are defined in the following in more detail.

The term "contacting" comprises all measures necessary to allow a chemical, biochemical or physical interaction between the MUC1 molecule and the antibodies used in the method. For this purpose the MUC1 molecules and the antibodies are preferably introduced into a suitable liquid. Suitable liquids are, e.g., buffer solutions which, as described in the prior art or the Examples, in ELISA or RIA detection systems or solutions described for chromatographic purification methods. Particularly suitable are solutions used in the prior art for affinity chromatography with antibodies. Suitable solutions are particularly preferably the solutions described in detail in the Examples.

The term "mixture of MUC1 molecules" comprises a large number of MUC1 molecules which can belong to the same or different species. As already stated before the MUC1 tumour markers described in the prior art are a mixture of different molecular species which differ as to their glycosylation and partly in their amino acid composition. The mixture of MUC1 molecules used in the inventive method may also contain further molecules, such as sugars, lipids, proteins or peptides which do not belong to the MUC1 group. Such mixtures of MUC1 molecules can preferably be obtained from tumour tissue, tumour cells as well as from cells or cell lines producing inter alia tumour-associated MUC1. In a particularly preferred manner lysates may be produced from these tissues, cells or cell lines. These cell lysates or fragments thereof may also serve as MUC1 mixtures within the meaning of the present invention. Synthetic glycopeptides or fragments of the tumour-associated MUC1 may also serve as mixture of MUC1 molecules. The preparation of synthetic glycopeptides is known from the prior art (Karsten, loc. cit.). Glycopeptides may also be produced by treatment with proteases and/or glycosidases from MUC1 preparations.

The term "antibody" within the meaning of the invention comprises murine, chimeric, humanized, human antibodies, whole antibodies of different isotypes or fragments of antibodies, such as single-chain antibody fragments (ScFv), Fab fragments, multivalent antibody fragments (e.g., diabodies, triabodies or tetrabodies), or antibody fragments of other formats, even such as are used as fusion proteins coupled with other peptides or protein structures, as well as antibodies or antibody fragments which, besides the specificity to MUC1 according to the present invention also have one or more further specificities, such as bispecific antibodies. The specificity according to the present invention of the antibodies according to the present invention is defined further below. These antibodies are produced by techniques known per se. The antibodies used in the method according to the present invention are characterized by the above mentioned properties.

In this connection the term "immunodominant region of the MUC1 tandem repeat" within the meaning of the present invention means the PDTR (SEQ ID NO:3) region which strictly speaking also comprises further amino acids of the adjacent sequences of the MUC1 tandem repeats, for example APDTRPAP (SEQ ID NO:4). Whether an antibody binds to this region can be readily determined by the skilled person by methods known from the prior art.

The term "MUC1 tandem repeat" designates a sequence of 20 amino acids: HGVTSAPDTRPAPGSTAPPA (SEQ ID NO:2). The five potential O-glycosylation sites on two serines and three threonines have been underlined in the previously shown sequence. Furthermore, in accordance with the present invention this term also comprises such variants which possess mutations and thus amino acid substitutions in one or more tandem repeats of a longer MUC1 molecule. The tandem repeat has 20 amino acids and may start in any place.

The term "unglycosylated MUC1 tandem repeats exist in series" designates a linear sequence of several tandem repeats of the MUC1, this sequence not being interrupted by other sequences. Preferably, there exist at least two, at least three, at least four or at least five tandem repeats existing in series. Most preferably there exist at least six tandem repeats in series.

The term "enhanced" within the meaning of the present invention means a binding of the antibody to a PDTR (SEQ ID NO:3)-glycosylated MUC1 peptide having between 9 and 40 amino acids that is significantly stronger than the binding to a corresponding peptide which is unglycosylated in the PDTR (SEQ ID NO:3) region. This applies for PDTR (SEQ ID NO:3)-glycosylated tandem repeats under the above item ii (ii—binding to an MUC1 fragment having a length of between 9 and 40 amino acids and containing sequences of the MUC1 tandem repeat and the immunodominant region is enabled or enhanced by glycosylation of the threonine of a PDTR (SEQ ID NO:3) sequence). This also includes a binding of the antibody to several tandem repeats in series which is significantly stronger than a binding to individual tandem repeats. This applies to unglycosylated tandem repeats under item iii) (binding to unglycosylated MUC1 tandem repeats is enhanced when the unglycosylated MUC1 tandem repeats exist in series;) and to PDTR (SEQ ID NO:3)-glycosylated tandem repeats under item iv) (iv)—the binding to multiple glycosylated MUC1 tandem repeats carrying glycosylations at the threonines of several PDTR (SEQ ID NO:3) sequences of the immunodominant region is enhanced vis-à-vis the short MUC1 fragments of ii) in view of an additive effect from their length and the PDTR (SEQ ID NO:3) glycosylation). Whether a binding is significantly enhanced may easily be determined by the skilled practitioner by suitable statistical tests and is shown in Examples 1 to 3.

The term "made possible" within the meaning of the present invention stands for the binding of an antibody to a PDTR (SEQ ID NO:3)-glycosylated MUC1 peptide having between 9 and 40 amino acids which is made possible by glycosylation at this site. Corresponding peptides which are not glycosylated at the PDTR (SEQ ID NO:3) region do not bind or the binding is hardly detectable with the methods used (see also 2).

The term "immune complex" within the meaning of the present invention means the product of an antibody-antigen reaction. Hereby the antibody reversibly binds to the antigen via physicochemical interactions. The interacting components form the immune complex.

The term "isolation" comprises all measures or methods which serve to separate the immune complex from antibodies which have not formed an immune complex with an antigen as well as from MUC1 molecules or other molecules which were not bound by an antibody. These methods are known in the art and described in the Examples. They comprise for example measures leading to the precipitation of the immune complex or chromatographic methods. Further methods are also described in more detail in the following.

In addition the invention describes a novel and unexpected tumour epitope on the whole molecule of MUC1 which can be prepared/obtained by the method of the invention. The novel MUC1 tumour epitope according to the present invention on the whole molecule of MUC1 is characterized by the combined binding specificities of MUC1-specific monoclonal antibodies of group 1 which in the following are described in detail. All analyzed monoclonal antibodies having the common binding properties described in the following, were generated by immunization of mice with MUC1 from tumour material.

Antibodies of group 1 have the common relevant binding properties 1 to 4:

1) The antibodies bind to the immunodominant region (so-called PDTR (SEQ ID NO:3) region—see definition) of the MUC1 tandem repeat.
2) The binding of the antibodies to an MUC1 fragment of the MUC1 tandem repeats containing the PDTR (SEQ ID NO:3) region and having a length between 9 and 40 amino acids is enabled or enhanced by glycosylation on the threonine of a PDTR (SEQ ID NO:3) sequence of the immuno-dominant region. The binding to the corresponding MUC1 peptides which are not glycosylated in the PDTR (SEQ ID NO:3) sequence is clearly lower. A glycosylation with Tn (GalNAcα1-O-Thr) is sufficient to achieve this effect, however a longer glycosylation as for example by TF (Galβ1-3GalNAcα1-O-Thr) is also possible to achieve this effect. Glycosylations on other glycosylation sites of the MUC1 tandem repeat have no or no significant influence on the basic effect (see Example 1 and Table 1).

3) The antibodies bind to unglycosylated MUC1 tandem repeats better if they exist in series. There the multiple unglycosylated MUC1 tandem repeat peptide comprises at least 3 tandem repeats, it being, however, also possible that the binding can only be strengthened by further tandem repeats and/or be strengthened even more significantly by an increased number of tandem repeats. With most antibodies the greatest increase in binding is found with MUC1 peptides having 4 tandem repeats to MUC1 peptides having 6 tandem repeats (see Example 2 and Table 2).

4) The antibodies show a binding property which in the invention is called an additive effect. The antibodies bind better to PDTR (SEQ ID NO:3)-glycosylated MUC1 tandem repeats when they exist in series. There the multiple PDTR (SEQ ID NO:3)-glycosylated MUC1 tandem repeat peptide contains at least 2 tandem repeats and at least 2 glycosylated PDTR (SEQ ID NO:3) regions. It is also possible that the binding is only strengthened by further PDTR (SEQ ID NO:3)-glycosylated tandem repeats and/or even more significantly increased by an increased number of PDTR (SEQ ID NO:3)-glycosylated tandem repeats. With many antibodies the greatest increase of binding is found with multiple PDTR (SEQ ID NO:3)-glycosylated MUC1 tandem repeat peptides of 4 tandem repeats to such of 6 tandem repeats (see Example 3 and Table 3).

The tumour epitope is described by the binding specificities of the antibodies which have the binding properties 1 and 2 and 3 and 4. Here preferred is the antigenic epitope structure which is bound by antibodies with particularly high additive effect, such as A76-A/C7 and VU-11E2, with A76-A/C7 being preferred. A further preferred form of the MUC1 tumour epitope according to the invention is the structure which is preferably bound by the antibodies having a particularly high additive binding effect, such as A76-A/C7, VU-11E2, with A76-A/C7 being preferred, since in colon carcinoma patients A76-A/C7 shows a significantly reduced binding to MUC1 released in serum (shedded MUC1). In contrast, HMFG-1 shows a significantly stronger binding in colon and pancreas carcinoma patients. This fact is a great advantage for immune therapies using MUC1 molecules or MUC1 specific antibodies with this specificity.

Since the effect of the length of antibodies vis-à-vis unglycosylated tandem repeats alone does not bring about a difference between antibodies prepared by immunization with tumour material and such antibodies prepared by immunization with non-tumour material, it becomes clear that the loop structure described in the literature which occurs in unglycosylated MUC1 peptides of multiple tandem repeats in the form described therein does not exactly correspond to the tumour epitope according to the present invention.

All tested antibodies from immunizations with MUC1 from tumour material show a binding property which is dependent on the glycosylation of the PDTR (SEQ ID NO:3) region, preferably with an MUC1 structure having a length of at least 9 amino acids and being surrounded by at least 3 additional amino acids around the PDTR (SEQ ID NO:3) region, and on that unglycosylated MUC1 tandem repeats exist in series. The majority shows the additive binding effect from multiple tandem repeats and PDTR (SEQ ID NO:3) glycosylation. In contrast, nearly all tested antibodies obtained by immunization with non-tumour material are independent on glycosylation. Most antibodies are negative for the additive effect.

Preferred antibodies for the definition according to the invention and description of the tumour epitope according to the invention and the use according to the invention of these antibodies for the diagnosis and treatment of tumours as well as to the preparation according to the invention of suitable MUC1 molecules for the treatment and diagnosis of tumour, are such antibodies from group 1 which have an additive binding effect from length and PDTR (SEQ ID NO:3) glycosylation, as described under binding property 4, for example A76-A/C7, VU-11E2, VU-11 D1, BC4E549, VU-12E1, VU-3D1 and b-12 (see Table 3; source of antibodies is disclosed in Table 1). These antibodies have an increased affinity to multiple tandem repeats and multiple PDTR (SEQ ID NO:3) glycosylated tandem repeats and to native tumour-MUC1 consisting of multiple tandem repeats, and are thus to be preferred according to the invention.

Particularly preferred are antibodies for the inventive definition and description of the tumour epitope and for the use according to the invention of these antibodies for the diagnosis and treatment of tumours as well as to the preparation according to the invention of suitable MUC1 molecules for the treatment and diagnosis of tumours, which have a pronounced additive binding effect. These antibodies bind to multiple PDTR (SEQ ID NO:3) glycosylated MUC1 tandem repeat peptides of 4) clearly to many times stronger than to short PDTR (SEQ ID NO:3) glycosylated MUC1 peptides of 2) and their binding to multiple unglycosylated MUC1 tandem repeats of 3). The antibodies of this preferred subgroup show a pronounced additive effect of binding enhancement by glycosylation of the PDTR (SEQ ID NO:3) sequence according to 2) and multimerisation of the tandem repeats according to 3) (see Example 3 and Table 3). The antibodies of this group, preferably A76-A/C7, VU-11E2 and VU-11D1 (see Example 3 and Table 3), show a particularly strong additive effect and have a particularly increased affinity to multiple PDTR (SEQ ID NO:3) glycosylated tandem repeats and thus to native tumour MUC1 which consists of multiple tandem repeats, and thus are preferred according to the present invention.

All tested MUC1-specific antibodies which have binding properties of group 1 correlate to the immunogen which was used for their generation in mice (see Example 2 and Table 1), for example in form of whole tumour cells or MUC1 obtained from tumour material. MUC1-specific monoclonal antibodies (mab) which were obtained from immunizations with non-tumour relevant MUC1 material, do not show this combination of binding properties. They are all independent or inversely (negatively) dependent on the glycosylation of the PDTR (SEQ ID NO:3) region according to 2) or independent from the length of the unglycosylated MUC1 peptides and thus the number of tandem repeats according to 3). This unexpected correlation shows that antibodies possessing the binding properties of group 1 recognize a specific antigenic structure on the MUC1 which corresponds to a novel tumour epitope on MUC1 and which is therefore particularly suitable as target structure for a tumour therapy and for diagnostic purposes. Therapeutic and diagnostic methods using this novel and unexpected tumour epitope as target structure, significantly improve previous approaches looking at the MUC1 according to its previously known tumour-associated properties overexpression, apolar expression and aberrant glycosylation.

The present invention describes a novel and surprising tumour epitope on the human polymorphic epithelial mucin MUC1. The invention claims this epitope as well as substances and methods for their preparation, which contain this epitope, such as cells, glycoproteins or glycopeptides, and methods for use in the prophylaxis and treatment of tumour diseases, including vaccines, such as whole cell vaccines, glycoprotein vaccines or glycopeptide vaccines, as well as antibodies obtained with the assistance of MUC1 as immunogen obtained by the production method according to the present invention, and which have an increased additive effect and are therefore particularly suitable for use in the treatment and/or diagnosis of tumour diseases.

For use of MUC1 in tumour therapy and prophylaxis it is necessary to isolate and/or identify such MUC1 molecules which bear tumour-relevant epitopes and have as far as possible no or at least a reduced immuno-suppressive influence. This also applies to the isolation and preparation of cells or other carrier substances which carry MUC1 molecules that are suitable according to the present invention. For diagnosis it is advantageous to obtain differential diagnostics with which it can be determined whether and to what degree MUC1 is present, which carries tumour-relevant epitopes or less relevant, respectively, irrelevant epitopes, and which does not have a reduced or increased immuno-suppressive effect (see also infra, diagnostics). The methods of the invention which are in the following described allow the definition, characterization and isolation of the above MUC1 molecules which are suitable according to the present invention.

The present invention relates to methods allowing the identification and/or generation of such MUC1 molecules or their fragments or derivatives which can advantageously be used in tumour treatment, tumour prophylaxis and tumour diagnosis, from the large pool of different MUC1 molecules, the structure of which is in no case chemically known in detail. Such MUC1 molecules are, according to the invention, designated in the following as tumour-associated MUC1 molecules, which in addition to molecules may also comprise molecule mixtures, such as glycopeptides, glycoproteins or mixtures thereof as well as fragments and derivatives of the molecules containing the tumour epitope of the present invention. According to the present invention, tumour-associated molecules are also cells and other carrier substances, such as viruses, bacteria, parts of cells, such as exosomes or cell lysates, or liposomes, which contain one or more tumour-associated MUC1-molecules with the tumour epitope according to the invention. The methods correspond to screening assays allowing to identify and obtain suitable MUC1 for the applications mentioned above and described below in detail. The central step of the method of production consists in the identification and/or isolation of tumour-associated MUC1 molecules by means of antibodies recognizing the MUC1 tumour epitope according to the present invention, such as antibodies of group 1 (A76-A/C7, VU-11E2, VU-11 D1, BC4E549, VU-12E1, VU-3D1 and b-12). A preferred group of antibodies are such antibodies which show an additive binding effect of length and PDTR (SEQ ID NO:3) glycosylation, such as A76-A/C7, VU-11E2, VU-11 D1, BC4E549, VU-12E1, VU-3D1 and b-12. A further preferred group of antibodies are antibodies with a particularly pronounced additive effect, such as A76-A/C7, VU-11E2 and VU-11D1. The antibody A76-A/C7 is preferred according to the present invention for all uses, since it has the most pronounced additive effect. A further antibody which is suitable for the method of production according to the present invention is VU-4H5, which also has a pronounced additive effect, but otherwise is inversely glycosylation-dependent with regard to short PDTR (SEQ ID NO:3)-glycosylated tandem repeats (see Example 4). This group also comprises other antibodies having comparable binding properties.

The individual methods used in the methods are known to the skilled person and, by way of example, are described in detail in the Examples.

In a method according to the present invention, tumour-associated MUC1 molecules are identified and/or isolated and obtained by binding to the above mentioned antibodies.

The methods used for identification are methods known per se, such as ELISA, RIA, Western Blot, Immune Precipitation, Scatchard Blot Analyses, FACS Analyses, MACS Analyses, immunocytochemistry and immunohistology. Most of these methods are described in detail in the Examples.

According to the method of the invention the above described MUC1 molecules may be obtained, as shown above, by affinity chromatography on one or more antibodies from body fluids, such as serum, breast milk or urine, or from supernatants of cell cultures. Further purification and/or concentration steps according to methods known per se can be combined with one or more affinity chromatography steps on the antibodies. Tumour-associated MUC1 molecules can likewise be obtained from tumour cells, tumour tissues or tumour cell lines, by first applying a suitable step according to methods known per se which makes the MUC1 bound to the cell membrane or intracellular MUC1 accessible to affinity purification, for example by solubilization with suitable detergents or by separation of extracellular MUC1 components by proteolysis or cell lysis. A differential purification of the tumour-associated MUC1 molecules from supernatants of cell cultures and from body fluids separated from membrane-bound tumour-associated MUC1 from tumour cells, tumour tissues or tumour cell lines is made possible by a combination of the above described methods. An important step hereby is the separation of supernatants and cells according to methods known per se, such as centrifugation. For the preparation of secreted and membrane-standing tumour-associated MUC1 molecules, a combination of both methods is used, for example by combining the cell culture supernatants with solubilized, membrane-standing MUC1 before carrying out corresponding affinity chromatography steps on suitable antibodies. Tumour-associated MUC1 molecules according to the present invention also include such that are further purified or first purified by further affinity chromatography steps with other tumour-specific antibodies, for example antibodies or lectins against tumour-associated or tumour-specific carbohydrate antigens, such as the Thomsen-Friedenreich antigen, the Tn antigen, the sialyl-Tn antigen or the Lewis Y-antigen, to generate tumour-associated MUC1 molecules carrying multiple tumour antigens. Such tumour-associated MUC1 molecules are advantageous for tumour therapy, since immune responses against the tumour excited thereby are more difficult for tumour escape mechanisms to circumvent.

Fragments of tumour-associated MUC1 molecules can be prepared by methods known per se before or after affinity chromatography on suitable antibodies, for example by enzymatic or chemical proteolysis, and purified by suitable methods known per se. Fragmentation may be preceded by partial deglycosylation, for example by one or more enzymatic deglycosylation steps, such as the complete or partial separation of sialic acids by sialidases, or the complete or partial separation of fucose components by one or more chemical deglycosylation steps, such as the per-se known TFMSA method (Trifluoromethylsulfonic acid treatment).

Tumour-associated MUC1 molecules and their fragments may be further modified according to methods known per se. Modifications according to the present invention may for example comprise the modification of the glycosylation in one or more steps, e.g., the enzymatic glycosylation or deglycosylation with glycosyl transferases and/or glycosylidases and/or chemical deglycosylations. The modifications can be made prior to or after affinity chromatography steps on antibodies. The resulting fragments may be further purified or fractionated by suitable purification and/or concentration steps according to methods known per se. Further modifications according to the invention comprise couplings with other substances, e.g., such as increase an immune response against MUC1 on tumour cells and/or favor an application for the treatment and/or prophylaxis of tumours and/or metastases in humans, e.g., coupling of the tumour-associated MUC1 molecules to carrier molecules, such as KLH, or to immunostimulating molecules, such as interleukins, GM-CSF, interferons and/or TNF-alpha, or such as increase the stability of the molecules in vivo and during storage, or such which increase an expression, or such which cause production-technological advantages, such as solubility. The couplings are made according to methods known per se, such as chemically via suitable spacers or biochemically in the form of recombinant fusion proteins expressed in cells (see infra), such as interleukin 12 or tetanus toxoid peptide.

A method for producing tumour-associated MUC1 molecules according to the present invention is also the synthesis of glycopeptides by methods known per se, which are better bound by the antibodies of the present invention which recognize the MUC1 tumour epitope than the identical glycopeptides which, however, are not glycosylated in the PDTR (SEQ ID NO:3) region. In this connection it may be advantageous to completely or partly synthesize tumour-associated MUC1 molecules obtained by one of the above described methods, and to couple them by one or more additional amino acids, such as cysteine or lysine and carrier molecules, to molecules known per se, such as KLH. A complete or partial analysis is made by methods known per se, for example the fragmenting mass spectrometrical analysis, such as PSD-MALDI-MS or ESI-MS/MS, or NMR or immunochemical methods.

MUC1 glycopeptides according to the present invention are obtained by synthesizing glycopeptides according to methods known per se and testing their binding to MUC1 antibodies. MUC1 glycopeptides bound by antibodies recognizing the MUC1 tumour epitope of the present invention and which bind them in a better way than the identical glycopeptides which, however, are not glycosylated at the PDTR (SEQ ID NO:3)-region correspond to the criteria according to the invention for MUC1 glycopeptides (the mentioned binding properties of these antibodies have already been described supra under item ii)). According to the invention such MUC1 glycopeptides are preferred that are better bound by antibodies than corresponding shorter glycopeptides having 1 or 2 tandem repeats but the same glycosylation and the same glycosylation sites (the mentioned binding properties of these antibodies have already been described supra under item iv)). In a preferred variant the peptide-chip technology is used. By it a large number of MUC1 peptides is prepared, which are glycosylated on different positions and/or have different lengths. By means of the binding of antibodies to the MUC1 tumour epitope according to the invention, such MUC1 glycopeptides are obtained by the HT method (high throughput) which meet the criteria for MUC1 glycopeptides according to the present invention. In a further preferred variant such MUC1 glycoproteins may be obtained by the same method which in addition are particularly immunogenic for carbohydrate epitopes, by additionally testing the above described peptide-chips with tumour-specific anti-carbohydrate-antibodies and identifying such glycopeptides which are bound by antibodies to the MUC1 tumour epitope according to the present invention and by antibodies to the tumour-specific carbohydrate antigen. The HT methods are basically known for peptides and may also be used for glycopeptides.

Methods for the preparation of structures carrying several to many tumour-associated MUC1 molecules are carried out in a manner known per se, for example by chemical coupling to liposomes or coupling to lipids and subsequent inclusion in liposomes or by coupling to other carrier structures.

As will be described in the following, also the methods according to the invention also make use of cells or cell lines carrying or secreting, or secreting and carrying MUC1 molecules or fragments thereof which may be prepared by the above described methods. Methods for preparing such cells include the selection of cells which carry the tumour-associated MUC1 molecules by binding to antibodies recognizing the tumour epitope (group 1, preferably A76-A/C7). For this, methods are used which are known per se. For example, the cells with tumour-associated MUC1 molecules are obtained by magnetic separation by means of particles binding to a magnet and loaded with the antibodies (MACS sorting) and separated from such cells which carry no or only small amounts of tumour-associated MUC1 molecules. A further example is the sorted extraction of the fluorescence-marked cells carrying the antibodies by means of a FACS sorter. Both methods are known to the skilled person. In this connection it is advantageous to clone by methods known per se the cells obtained by antibody-binding by individualization (limiting dilutions) in suitable media according to methods known per se, in order to obtain stable cell clones and to identify and select via antibody-binding, e.g., by means of quantitative ELISA according to methods known per se, which cell clones secrete, carry or carry and secrete a suitable amount of tumour-associated MUC1 (see Example 5). A part of the production method is preferably a quantitative sandwich ELISA which is explained infra in detail (test method quantitative sandwich ELISA; see Example 5). An alternative method which may also be complementary used is the quantitative determination of the MUC1-positive cells and the amount of tumour-associated MUC1 molecules on the cells via a FACS analysis or a Scatchard blot analysis known per se to the person skilled in the art, by means of the antibodies according to the invention, which recognize the MUC1 tumour antigen.

The cells or cell lines are either used themselves as tumour-associated MUC1 molecules in the applications of the invention or secreted or membrane-standing or secreted and membrane-standing glycoproteins, glycopeptides, or their fragments, are obtained from the cells according to the above described methods of the invention. Cell lysates, too, are prepared according to the invention by methods known per se, such as by alternative freezing with liquid nitrogen and thawing.

A further method for producing cells or cell lines according to the invention in addition to the above mentioned methods comprises a transformation of cells with recombinant MUC1. For this suitable cells or cell lines are selected and either the expression of MUC1 is increased, novel forms, e.g., fragments, of the MUC1 are expressed or MUC1 is expressed de novo with the aim of obtaining tumour-associated MUC1 molecules or obtaining cells carrying or secreting more or improved tumour-associated MUC1 molecules. For this the MUC1 gene or parts thereof are used. Preferably, the MUC1 gene comprises a DNA sequence selected from the group of sequences deposited at NCBI consisting of: Deposition Nos. NM 002456, XM 053256, AF125525, AF348143, S81781, X80761, X69118, J05582 and M21868. Preferred are such parts of the MUC1 gene which code for shortened versions containing one or more tandem repeats, cloned in a suitable expression vector by methods known per se and introduced into the cells, e.g., by electroporation. The transformed cells are selected according to methods known per se, e.g., via selection with suitable antibiotics, the resistances of which are also encoded on the recombinant genetic material introduced (see Example 5). Stably transformed cells are preferred, as described above, cloned, for example by limiting dilution, preferably in combination with an enrichment of the cells expressing the tumour-associated MUC1 molecules, e.g., by FACS or MACS (see Example 5).

In a further method according to the invention, tumour-associated MUC1-molecule positive cells or cell lines are made sensitive by gene transfer to the treatment of cytostatic drugs, e.g. by the insertion of the HSV-TK gene, which causes the cells to become sensitive for a ganciclovir treatment. The genes are inserted and the transformed cells are selected by methods known per se. According to the present invention, the ganciclovir-sensitive cells are killed by ganciclovir either by their application on humans or after application on humans. This method allows to control living cells or cell lines applied in tumour treatment to humans and is used for this purpose alternatively or complementary to the radiation of cells (see also uses of the present invention).

In a further method according to the present invention, tumour-associated MUC1 molecules are obtained from tissues by generating the tumour-associated MUC1 molecule by means of the techniques described above from the cell membranes. For this, the tissue is broken down by methods known per se to make the membrane-standing tumour-associated MUC1 molecules accessible, e.g., by proteolytic or mechanical methods.

The methods are explained in more detail in the Examples, but are not limited thereto.

By means of the production methods, tumour-associated MUC1 molecules may be obtained which have no or only a reduced immunosuppressive effect and which generate an immune response to the native tumour-MUC1 and to tumour cells. It is shown in Example 5 how tumour-associated MUC1 molecules according to the present invention have no or a reduced immunosuppressive effect. Such tumour-associated MUC1 molecules of the invention are immunogen and can produce an anti-tumour immune response.

Preferably, one part of the production method is a quantitative Sandwich ELISA in which an anti-MUC1 antibody is immobilized, cells or MUC1 obtained from supernatants or membrane preparations are applied in suitable solutions and detected by a second anti-MUC1 antibody. At least one antibody is directed to the tumour-associated MUC1 molecule of the invention. The second antibody is preferably directed to an epitope of MUC1 which does not lie in the PDTR (SEQ ID NO:3) region or to a carbohydrate epitope, such as the Thomsen-Friedenreich antigen. According to the present invention, this quantitative Sandwich ELISA is a test procedure for the preparation of tumour-associated MUC1 molecules, including cells, as well as a test procedure for diagnosis.

To some extent, antibodies to MUC1 are already used for diagnosis and clinically studied for the treatment of tumours. However, the MUC1-specific antibodies recognize different epitopes on MUC1, which has a large number of different epitopes and, moreover, as described above, is not an exactly structurally defined molecule but a heterogeneous mixture of molecules, which differs from tumour to normal tissue, for example in its glycosylation. Thus, at present the HMFG-1 is under clinical study, which does not recognize the MUC1 tumour epitope of the present invention.

The invention shows which antibodies in view of their binding properties are advantageous for the treatment of tumours. Thus the invention allows the selection of better suitable antibodies for the tumour treatment in form of a screening procedure (screening assay): The invention provides a method for the determination of the suitability of antibodies for the treatment of tumours and for diagnosis and for recognizing the tumour epitope of the invention. This method comprises a combination of biochemical tests, which are described in Examples 1 and 2, and preferably also in 3. As described above, antibodies possessing the binding properties defined in group 1 or of Example 4 in the method, are suitable within the meaning of the invention. By means of this procedure, also antibodies are characterized and obtained which are suitable to determine the MUC1 tumour epitope of the invention and which are suitable to characterize, isolate and obtain tumour-associated MUC1 molecules of the present invention.

Furthermore, the invention provides a method for preparing particularly suitable monoclonal antibodies for therapy and diagnosis of tumour diseases, since they have a particularly pronounced additive effect compared to previously tested antibodies. The method of the invention comprises the immunization of animals or humans with MUC1 material in form of molecules, cells or cell lysates, which material was obtained with the method of the present invention. The antibodies are produced and characterized by methods known per se, including at least one of the above described test systems. The specificity of the antibodies is tested for particularly high additive effects.

Advantageously, the methods of the present invention allow the preparation or identification of tumour-associated MUC1 molecules which are able to produce an immune response in humans, and thus are suitable starting substance for vaccines against tumours which produce tumour-associated MUC-1. The preparation of these MUC1 molecules has only become possible by the methods of the present invention. The present invention is based, inter alia, on the surprising finding that antibodies produced in mice to tumour-associated MUC1 which possess the above described properties are able to specifically bind in the heterogeneous group to such tumour-associated MUC1-molecules which are able to trigger an immune response in humans, as can be shown for example in NOD-SCID mouse test. These MUC1 molecules are preferably characterized by having an increased number of epitopes having an immunostimulating effect and a reduced number of or no immunosuppressive epitopes at all.

The definitions introduced above of the terms are also applicable mutatis mutandis for the terms used in the following methods.

The present invention furthermore comprises a method for identifying an MUC1 molecule which is able to trigger an immune response in humans, comprising:
a) contacting a mixture of MUC1 molecules with an antibody having the following properties:
 i) binding to the immunodominant region of the MUC1 tandem repeat; and
 ii) binding to an MUC1 fragment having a length of between 9 and 40 amino acids and containing sequences of the MUC1 tandem repeat and the immunodominant region is made possible or enhanced by glycosylation of the threonine of a PDTR (SEQ ID NO:3) sequence; and iii) binding to unglycosylated MUC1 tandem repeats is enhanced when the unglycosylated MUC1 tandem repeats exist in series; and iv) binding to multiple glycosylated MUC1 tandem repeats carrying glycosylations on the threonines of several PDTR (SEQ ID NO:3) sequences of the immunodominant region is increased due to an additive effect of length and PDTR (SEQ ID NO:3) glycosylation vis-à-vis short MUC1 fragments of ii)

for a period of time sufficient and under conditions suitable to allow the formation of an immune complex; and b) identification of the immune complex.

The term "identifying" within the framework of the invention comprises all measures by which an immune complex can be detected. Suitable procedures are known from the prior art and comprise for example ELISA, MACS, RIA, Scatchard blot analysis, Western blot, immunocytochemistry, immunohistology or FACS methods. Suitable procedures are described in more detail also in the following.

In a preferred embodiment the methods of the invention further comprise at least one of the following steps:

1) Obtaining the MUC1 molecule or a mixture thereof in step (a) of the method of the invention from tumour tissue, tumour cells and/or body fluids containing tumour-associated MUC1 molecules, which had been previously isolated;

2) obtaining the MUC1 molecule or a mixture thereof in step (a) of the method of the invention from cells or cell lines expressing and/or secreting tumour-associated MUC1 molecules or mixtures thereof;

3) obtaining the MUC1 molecule or a mixture thereof in step (a) of the method of the invention from recombinant cells or cell lines previously modified by genetic engineering in such a way that they express and/or secrete tumour-associated MUC1 molecules or mixtures thereof;

4) obtaining the MUC1 molecule or a mixture thereof in step (a) of the method of the invention from cell lysates and/or the cell supernatant from tumour tissue, tumour cells and/or body fluids as described under (1) or from cells or cell lines as described under (2) and (3), which contain tumour-associated MUC1.

Suitable tumour tissues or tumour cells can be obtained from tumour patients or persons without tumour, in the latter case, a further treatment, as described elsewhere, may be necessary, such as partial deglycosylation prior to affinity purification.

A preferred embodiment of the present invention are tumour-associated MUC1 molecules in the form of glycoproteins or glycopeptides, which were obtained from the supernatant of cells which secrete a large amount of tumour-associated MUC1 molecules. In the preferred method of the present invention a subcell line of the mammary carcinoma cell line ZR-75-1 by means of ELISA techniques, FACS analyses and immunocytochemical tests identified and characterized as suitable cell line, which express tumour-associated MUC1 molecules on the surface and secrete them into the cell culture supernatant, see also Example 5. Since the expression rate of the individual cells varies, clones (sublines) were prepared from the starting cell line by limiting dilution, which clones carry and/or secrete stably increased amounts of tumour-associated MUC1 molecules, see also Example 5. In a further preferred procedural step of the invention the MUC1 gene or parts thereof were integrated into the cell by an expression vector and procedure more closely described in Example 5 in order to further increase the expression of the secretory tumour-associated MUC1 molecules. The cells were again cloned by limiting dilutions in suitable culture media. From the resulting sublines tumour-associated MUC1 molecules are obtained from the supernatant by means of affinity chromatography on A76-A/C7, which are used in the methods of the invention as tumour agents in tumour treatment and in tumour diagnosis.

In a further preferred procedure, fragments are produced from the obtained tumour-associated molecules by limited proteolysis with clostripain according to methods known per se.

In a further preferred procedure, tumour-associated MUC1 glycopeptides are synthetically produced by methods known per se. These MUC1 glycopeptides are bound to antibodies recognizing the MUC1 tumour epitope of the present invention, and which bind them better than the identical glycopeptides which, however, are not glycosylated on the PDTR (SEQ ID NO:3) region. According to the invention, MUC1 glycopeptides are preferred which are better bound by antibodies than corresponding shorter glycopeptides having 1 or 2 tandem repeats but the same glycosylation and the same glycosylation sites. The corresponding binding properties have already been described above.

The method of the invention for use on humans comprises suitable pharmaceutical formulations, preferably in combination with adjuvants and/or co-stimulatory molecules, such as GM-CSF and in case of shorter MUC1 glycopeptides a coupling to KLH. A preferred variant is the loading of dendritic cells or cells possessing an immunostimulatory function comparable to dendritic cells, with cell lysates, or the fusion of cells carrying the tumour-associated MUC1 molecule I with dendritic cells according to procedures known per se, and the administration of these cells, preferably after radiation, to humans according to methods known per se. The treatment with loaded dendritic cells and glycopeptides and/or glycoproteins is preferably combined, later boostering being preferably carried out with the glycopeptides and/or glycoproteins of the invention in suitable pharmacological formulations according to the invention, preferably with adjuvants or co-stimulatory molecules (such as GM-CSF).

The preferred use according to the invention of the glycopeptides and glycoproteins or of the dendritic cells loaded with glycopeptides and/or glycoproteins is for the treatment and prophylaxis of MUC1-positive tumour diseases, such as mammary carcinoma, ovarian carcinoma, colon carcinoma, gastrointestinal carcinoma, pancreas carcinoma, lung carcinoma, multiple myeloma, and against primary tumours, minimal residual tumour diseases, metastases and as adjuvant treatment. Preferably, the glycopeptides and glycoproteins or the dendritic cells loaded with glycopeptides and/or glycoproteins are administered subcutaneously, intradermally, intrarectally, intranodally (lymph nodes) or systemically by procedures known per se.

The present invention also relates to a method for producing cells which comprise an MUC1 molecule capable of generating an immune response in humans, comprising:

a) contacting a mixture of cells containing MUC1 molecules with an antibody having the following properties:

i) binding to the immunodominant region of the MUC1 tandem repeat, and ii) binding to an MUC1 fragment having a length of between 9 and 40 amino acids and containing sequences of the MUC1 tandem repeat and the immunodominant region is made possible or enhanced by glycosylation of the threonine of a PDTR (SEQ ID NO:3) sequence; and iii) binding to unglycosylated MUC1 tandem repeats is enhanced when the unglycosylated MUC1 tandem repeats exist in series; and iv) binding to multiple glycosylated MUC1 tandem repeats carrying glycosylations on the threonines of several PDTR (SEQ ID NO:3) sequences of the immunodominant region is increased due to an additive effect of length and PDTR (SEQ ID NO:3) glycosylation compared to short MUC1 fragments of ii)

for a period of time sufficient and under conditions suitable to allow the formation of an immune complex;

b) isolation of the cells which have formed an immune complex; and c) making the cells from the immune complex available.

The term "cells which comprise an MUC1 molecule capable of generating an immune response in humans" comprises all cells which produce a tumour-associated MUC1 molecule as described above. Such cells are preferably cells which can be isolated or prepared from tumour tissue, tumour cell lines, or cells or cell lines, modified by genetic engineering in such a way that they produce a tumour-associated MUC1 molecule as described above. The last mentioned cells or cell lines may be produced by methods known from the prior art. These methods comprise for example procedures with which foreign DNA can be stably or transiently inserted into the cells or cell lines. In the following, further suitable procedures are also described in more detail.

The term "isolation of the cells" means all measures for the separation of cells which have formed an immune complex with antibodies due to the tumour-associated MUC1 molecules produced by them. The skilled person knows these methods. The preferred method for this is the FACS or the MACS method. In the following, further suitable methods are described in more detail.

The previously introduced definitions of the terms are applicable mutatis mutandis to the terms used in the below described methods.

The present invention further comprises a method for the identification of cells comprising an MUC1 molecule capable of generating an immune response in humans, comprising:

a) contacting a mixture of cells comprising MUC1 molecules with an antibody having the following properties:
  i) binding to the immunodominant region of the MUC1 tandem repeat, and
  ii) binding to an MUC1 fragment having a length of between 9 and 40 amino acids and containing sequences of the MUC1 tandem repeat and the immunodominant region, is made possible or enhanced by glycosylation of the threonine of a PDTR (SEQ ID NO:3) sequence; and
  iii) binding to unglycosylated MUC1 tandem repeats is enhanced when the unglycosylated MUC1 tandem repeats exist in series; and
  iv) binding to multiple glycosylated MUC1 tandem repeats carrying glycosylations on the threonines of several PDTR (SEQ ID NO:3) sequences of the immunodominant region, is increased due to an additive effect of length and PDTR (SEQ ID NO:3) glycosylation as compared to short MUC1 fragments of ii) for a period of time sufficient and under conditions suitable to allow the formation of an immune complex; and b) identification of the immune complex.

In a preferred embodiment the methods of the invention further comprise at least one of the following steps:

1) Obtaining of cells, cell lines or subcell lines carrying and/or secreting tumour-associated MUC1 molecules or mixtures thereof in step (a) of the method of the invention from tumour tissue or tumour cells containing tumour-associated MUC1 molecules, which had been previously isolated, with or without subsequent cell cloning;

2) obtaining of cells, cell lines or subcell lines carrying and/or secreting tumour-associated MUC1 molecules or mixtures thereof in step (a) of the method of the invention from cells or cell lines comprising tumour-associated MUC1 molecules, with or without subsequent cell cloning;

3) obtaining of cells, cell lines or subcell lines carrying and/or secreting tumour-associated MUC1 molecules or mixtures thereof in step (a) of the method of the invention from recombinant cells or cell lines previously modified by genetic engineering in such a way that they express and/or secrete tumour-associated MUC1 molecules or mixtures thereof, with or without subsequent cell cloning;

4) obtaining of cells, cell lines or subcell lines carrying and/or secreting tumour-associated MUC1 molecules or mixtures thereof in step (a) of the method of the invention, which were modified by genetic engineering in such a way that they carry and/or secrete immunostimulatory molecules, with or without subsequent cell cloning;

5) obtaining of cell lysates or mixtures of cell lysates from cells, cell lines or subcell lines as described under (1) to (4) above, which contain tumour-associated MUC1.

In a further preferred embodiment of the methods for the present invention, the antibody is selected from the group comprising A76-A/C7, VU-11E2, VU-11 D1, BC4E549, VU-12E1, VU-3D1 and b-12. Particularly preferred is the antibody A76-A/C7 and recombinant forms thereof, as will be described below in more detail. In a further embodiment of the method of the present invention the antibody is VU-4H5.

The antibody A76-A/C7 recognizes the MUC1 tumour epitope and has a particularly strong additive effect. Compared to the HMFG-1 which is undergoing clinical development, the A76-A/C7 according to the invention has a number of advantages: The A76-A/C7 recognizes the MUC1 tumour epitope of the present invention and was prepared as immunogen by means of a desialinated mammary carcinoma cell line (T47D). In contrast, HMFG-1 does not recognize the MUC1 tumour epitope of the invention and was prepared as immunogen by means of MUC1 from human milk (see also Examples 1 to 3). A76-A/C7 for example clearly distinguishes normal tissue and benign adenoma (negative) from malignant colon tumours such as carcinoma in-situ, carcinoma and metastases (strongly positive), whereas HMFG-1 does not make this clear differentiation. A76-A/C7 is a good serum marker for tumour diagnosis, whereas HMFG-1 is not suitable as serum tumour marker to the same degree. Moreover, the affinity of the A76-A/C7 is higher by a multiple than that of HMFG-1. Thus, compared to the HMFG-1 presently in clinical development, A76-A/C7 constitutes a significant improvement for applications according to the present invention.

The present invention also relates to a method for preparing an antibody comprising:

(a) carrying out the steps of the production and identification methods described above;

(b) inserting the MUC1 molecule, the cell or the cell lysates into an animal; and
(c) providing an antibody specifically recognizing the MUC1 molecule and showing a particularly pronounced additive effect.

In this context the expression "particularly pronounced additive effect" is to be understood as meaning that the increase of the binding of the antibody to multiple PDTR (SEQ ID NO:3)-glycosylated tandem repeats as described under 4) compared to short PDTR (SEQ ID NO:3)-glycosylated MUC1 peptides as described under 2), and both compared to not PDTR (SEQ ID NO:3)-glycosylated short MUC1 peptides is stronger than the increases of the binding of the antibodies A76-A/C7, VU-11E2, VU-11 D1, BC4E549, VU-12E1, VU-3D1 and b-12 (or comparable to the strongest increases of these antibodies).

The definitions of the terms given above apply mutatis mutandis to these and the following embodiments.

The term "antibodies" as used according to the present invention comprises:

murine, chimeric, humanised, human antibodies whole antibodies of various isotypes or antibody fragments, such as single-chain antibody fragments (ScFv), Fab fragments, multivalent antibody fragments (e.g., diabodies, triabodies, tetrabodies), or antibody fragments of other formats, including those used as fusion proteins coupled with other peptides or protein structures.

antibodies or antibody fragments which beside the specificity for MUC1 according to the present invention also possess one or more further specificities, e.g. bispecific antibodies.

molecules which strictly speaking are not antibodies, but which possess binding properties identical to those of the antibodies according to the present invention which carry the MUC1 tumour epitope, and/or parts of antibodies, such as CDR regions or fragments thereof, such as affibodies or other carrier structures carrying binding domains for specific binding. The invention also relates to antibodies derived from the antibodies here described and which thus acquire, increase an additive binding effect and/or bind better to the multiple PDTR (SEQ ID NO:3)-glycosylated tandem repeats than the starting antibody. The corresponding derivation of the antibody may result from methods known per se by deliberate or accidental modifications of the antibody and is tested by means of the comparing binding to corresponding MUC1 glycopeptides as described under Examples 1 to 3.

These antibodies are provided by techniques known per se. The antibodies may be obtained as polyclonal antibodies directly from the serum of the animals or by the known methods for producing monoclonal antibodies as such (Example 6).

The antibodies prepared by the method of the invention may advantageously be used against the MUC1 tumour epitope for the treatment of tumour diseases. These antibodies can be directly utilized in the treatment or prophylaxis of tumour diseases according to the present invention or coupled with effector structures. Effector structures according to the invention mean such chemical or biochemical compounds, molecules or atoms, which directly or indirectly cause the killing or harming, including for example the slowdown or inhibition of the growth of tumour cells. These include for example: radioisotopes, toxins, cytostatica and other effector molecules, such as cytokines and chemokines or other structures which themselves are effectors or are coupled to the effector molecules, for example liposomes loaded with toxins or cytostatica, which carry MUC1 antibodies. In the latter example, also such effector structures are meant which in addition to the MUC1 antibody for the tumour specificity also carry such molecules which are responsible for the reception of the effector structures or fragments thereof in the cells, such as antibodies to receptors causing receptor-mediated endocytosis and thus improving the MUC1-mediated reception. The combination of the antibodies with the effector structures is effected by methods known per se. The couplings may for example be directly effected by covalent or non-covalent loading, by chemical coupling, in which an additional chemical or biological molecule may be necessary, such as a chelator or a linker, or by fusion in the form of fusion proteins or fusion peptides.

The antibodies are used in the treatment of tumour diseases with MUC1-carrying tumour cells or for prophylaxis, which for example prevents the formation of primary tumours or metastases. Here, the preferred goal is the treatment of the minimal residual diseases and of metastases. The antibodies of the invention are administered in a suitable formulation one time or repeatedly at suitable intervals and dosages. A preferred form are radioactively labelled antibodies. A further preferred form are radioactively labelled diabodies, triabodies and tetrabodies. Further preferred forms are radioactively labelled single chain-antibody fragments and chimeric antibodies. However, the invention is not limited to these antibodies, the radioactive labelling and these antibody formats.

In the method of the invention for tumour diagnosis and prognosis, MUC1-specific antibodies recognizing the tumour epitope of the invention are utilized in methods known per se to detect MUC1 in serum or in tissue preparations. According to the invention free MUC1, MUC1 present in immune complexes and MUC1 bound on cells is detected and the presence of the tumour-associated MUC1 molecules is determined qualitatively, quantitatively and/or in relative quantities by methods known per se. The same methods are used according to the invention also for the development control of tumour diseases and for the control of the development of the treatment. The methods used in the procedures are known per se, e.g., ELISA, Western blot, FACS (fluorescence-activated cell sorting), MACS (magnetic cell sorting), ADCC (antibody-dependent cell-mediated cytotoxicity), CDC (complement-dependent cytotoxicity), immunocytochemistry and immunohistochemistry. An example for this is the Sandwich ELISA of the invention described further below with the antibodies described there and methods described in the examples. In a preferred method, antibodies, which recognize the tumour epitope of the invention, are compared with such antibodies which do not recognize the tumour epitope, to improve differentiation and evaluation. This serves to diagnose MUC1-positive tumours, to monitor the course of the tumour disease and to make a prognosis. The binding of the antibodies also determines the ratio of immunosuppressive MUC1, since MUC1 which is bound by antibodies against the tumour epitope of the invention does not have any or only a reduced immunosuppressive effect and in suitable formulations can specifically activate the immune system against tumour-MUC1.

In a method of the invention the antibodies recognizing the tumour epitope of the invention and such as are prepared by the method of the invention are used for in-vivo diagnosis. For this, the antibodies are labelled by suitable methods known per se and are thus made available for imaging methods on humans known per se, such as radioimmunodiagnosis, PET scan process or immunofluorescendoscopy, for example by coupling and/or loading with corresponding molecules, such as radioactive isotopes, e.g., indium, or fluorescent dye stuffs such as Cy3, Cy2, Cy5 or FITC.

The present invention further relates to a method for producing a pharmaceutical composition comprising the steps of the method of the invention and further comprising the steps of formulating the MUC1 molecule, the cell, the cell lysates or the antibodies or combinations thereof in pharmaceutically acceptable form.

The term "pharmaceutical composition" according to the invention defines substances and preparations of substances intended to heal, relieve or prevent by application on or in the human body, diseases, suffering, physical injuries or abnormal complaints. During the production process of the invention, medicinal and/or pharmaco-technical excipients may be added to the compounds identified by the methods of the invention. According to the present invention, medicinal excipients are such substances which are used for the production (as active ingredients) of pharmaceutical compositions in a method according to the present invention. Pharmaco-technical excipients merely serve to suitably formulate the pharmaceutical and may even be subsequently removed if they are only necessary during the process, or they may form a part of the pharmaceutical composition as pharmaceutically acceptable carriers. Examples for pharmaceutically acceptable carriers are given below.

The pharmaceutical may be formulated optionally in combination with a pharmaceutically acceptable carrier and/or diluent.

Examples for suitable pharmaceutically acceptable carriers are known to the skilled person and comprise phosphate-buffered saline solutions, water, emulsions, such as oil/water emulsions, different kinds of detergents, sterile solutions, etc. Pharmaceutical compositions comprising such carriers can be formulated by conventional methods. These pharmaceutical compositions can be administered to an individual in a suitable dosage, e.g., in a range from 1 µg to 100 mg per day and patient. The administration may be carried out in different ways, e.g., directly to the skin, intravenously, intraperitoneally, subcutaneously, intramuscularly, locally or intradermally. The administration of nucleic acids can also be made in the form of gene therapy. The kind of dosage is decided by the physician in charge depending on the clinical factors. The skilled person knows that the type of dosage depends on various factors such as the size, the body surface, the age, the gender or the general health of the patient, but also depending on the specific drug which is administered, the duration and kind of administration and on other medicaments which may possibly be administered in parallel.

Tumour pharmaceuticals according to the present invention comprise a pharmacological substance containing one or more tumour-associated MUC1 molecules according to the invention, cells comprising these or cell lysates prepared from these cells in a suitable solution or dosage form. These may be administered either alone or in combination with one or more adjuvants or another suitable substance for intensifying the effectiveness. The preferred adjuvants used are QS-21, GPI-0100 or other saponins, water-oil emulsions, such as montanide adjuvants, polylysine, polyarginine compounds, DNA compounds, such as CpG, Detox, bacterial vaccines, such as typhus vaccine or BCG vaccines, and are mixed in a suitable manner according to procedures known per se with the tumour-associated MUC1 molecules of the invention and/or with the antibodies. The tumour pharmaceuticals are produced by methods known per se. According to the present invention a tumour pharmaceutical is also a combination of 2 or more of the tumour pharmaceuticals of the invention, as well as a combination with other tumour vaccines or tumour treatments, such as antibody therapies, chemotherapies or radiotherapies, which in a suitable manner may be administered or used simultaneously or separately. The tumour pharmaceuticals are prepared by methods known per se.

According to the present invention, the tumour pharmaceuticals are used for the treatment of MUC1-positive tumour diseases, such as mammary carcinomas, ovarian carcinomas, colon carcinomas, gastrointestinal carcinomas, pancreas carcinomas, lung carcinomas, multiple myeloma. The treatment may also be an adjuvant treatment for example against primary tumours, minimal residual tumour diseases, metastases. According to the present invention, the tumour pharmaceuticals are used also for the prophylaxis of MUC1-positive tumour diseases. The prophylactic use aims for example to the prophylaxis of the tumour as well as of metastases. The tumour pharmaceuticals are administered in a suitable form by methods known per se. A preferred variant is the injection or administration of the tumour vaccines subcutaneously, intradermally, systemically, intravenously, intraperitoneally, intrarectally, locally into body cavities, such as the peritoneum, or locally directly into organs or lymph nodes. Preferably, different forms of administration may also be combined, wherein they can be administered on different days of treatment or on one treatment day. According to the invention, also 2 or more of the tumour pharmaceuticals of the invention may be combined or one or more of the tumour pharmaceuticals of the invention with one or more tumour pharmaceuticals or tumour treatments, such as antibody therapies, chemotherapies or radiotherapies which can be administered or used simultaneously or separately.

The method of the invention also comprises the production of a tumour pharmaceutical containing a cell vaccine obtainable by the loading of dendritic cells according to methods known per se with the tumour-associated MUC1 molecules of the present invention, and optionally by subsequent maturing of the cells. The resulting cell vaccine may be administered according to methods known per se. For example, to immature dendritic cells are added in a manner known per se tumour-associated MUC1 molecules. The dendritic cells receive the tumour-associated MUC1 molecules, process them and present fragments thereof on their surface in context with MHC molecules and co-stimulatory molecules. After a further maturing according to methods known per se, the cells are used on humans in a suitable formulation. A further example is the loading of the mature dendritic cells according to the known methods of pulsing. Dendritic cells are autologous, allogenic or semiallogenic dendritic cells or their precursor cells or cells from cell lines possessing the functional properties of dendritic cells, which are subjected ex vivo according to methods known per se to a suitable treatment for their development and maturing. The preparation of these tumour vaccines with suitable dendritic cells and MUC1 molecules according to the invention, cells or cell lysates, is carried out by methods known per se (see Example 7). According to the present invention, a further variant of the tumour pharmaceuticals consists in a T-cell therapy, in which T-cells recognizing suitable tumour-associated MUC1 molecules according to the invention, including fragments or processed derivatives thereof, which correspond to those by processing and presentation in vivo, in the context with MHC class molecules and co-stimulatory molecules and which are activated during presentation via suitable antigen-presenting cells. The preparation of such T-cell therapies is carried out according to methods known per se (see Example 7).

In a particularly preferred embodiment of the method of the present invention, cell lysates of cells enriched for tumour-associated MUC1 molecules on the cells, are prepared and utilized in the here described applications in tumour treatment and tumour prophylaxis. The methods of the invention for use on humans comprise suitable pharmaceutical formulations, preferably in combination with adjuvants and/or co-stimulatory molecules, such as GM-CSF. Here, a preferred variant is the loading of dendritic cells or cells possessing an immunostimulatory function like dendritic cells, with cell lysates, and the administration of these cells, preferably after radiation, to humans, according to methods known per se. The treatment with loaded dendritic cells and cell lysates is preferably combined, with later boosterings preferably carried out with cell lysates in suitable pharmaceutical formulations of the invention, preferably with adjuvants or co-stimulatory molecules (such as GM-CSF).

According to the invention, the preferred use of the cell lysates or the dendritic cells loaded with cell lysates is for the treatment and prophylaxis of MUC1-positive tumour diseases, such as mammary carcinomas, ovarian carcinomas, colon carcinomas, gastrointestinal carcinomas, pancreas carcinomas, lung carcinoma, multiple myeloma, and thereby against primary tumours, minimal residual tumour diseases, metastases, and as adjuvant treatment. The cell lysates or the dendritic cells loaded with cell lysates are preferably administered subcutaneously, intradermally, intrarectally, intranodally (lymph nodes) or systemically by methods known per se.

The definitions of the terms introduced above may be applied mutatis mutandis to the terms used in connection with the following embodiments.

The present invention furthermore relates to a method of preparing a diagnostic drug comprising the steps of the methods of the invention and further comprising the step of the formulation of the MUC1 molecule, of the cell, of the cell lysates or the antibodies in a diagnostically usable form.

According to the invention, the term "diagnostic drug" defines substances and preparations from substances aimed at recognizing by application on or in the human body or parts thereof, diseases, sufferings, physical injuries or abnormal complaints. The parts of the human body preferably mean body tissue samples or body fluids, such as blood, lymph, urine, spinal fluid or semen, or tissue biopsies. The formulation of the diagnostic drug preferably comprises the modification of the prepared MUC1 molecules with substances allowing the detection of the molecule. Suitable substances are known from the prior art. On the basis of the chosen substance, the person skilled in the art is able to use suitable measures for formulating the diagnostic drug.

According to the invention, for the diagnosis, substances can also be coupled to the tumour-associated MUC1 molecules according to methods known as such, which facilitate the detection of MUC1-specific antibodies, for example by means of biotinylation of the tumour-associated MUC1 molecules and subsequent immobilisation on ELISA plates.

In a further method for the diagnosis and prognosis of tumours according to the invention, tumour-associated MUC1 antibodies according to the invention are used which carry the tumour epitope, for the determination of MUC1 antibodies in the serum of humans, which recognise the tumour epitope. In a preferred method, MUC1 molecules or fragments thereof carrying the tumour epitope of the invention are used in comparison with antibodies not carrying the tumour epitope in order to achieve a better differentiation and assessment. In this context, according to the invention, free antibodies and antibodies present in immune complexes are detected and their specificities against the MUC1 tumour epitope according to the invention and, preferably other epitopes on the MUC1, including carbohydrate antigens, are determined qualitatively, quantitatively and/or in relative quantities according to methods known per se. According to the invention, the same methods are also used to monitor the course of tumour diseases and to monitor the course of treatments including monitoring of immune responses, for example IgG- and IgM-antibody responses against different epitopes including the MUC1 tumour epitope on MUC1, for the control and dosage of tumour treatment. The methods used in the processes are known per se, for example ELISA, Western blot, FACS (fluorescence-activated cell sorting), MACS (magnet cell sorting), ADCC (antibody-dependent cell-mediated cytotoxicity), CDC (complement-dependent cytotoxicity), immunocytochemistry and immunohistochemistry. One example thereof are glycopeptides coupled to a carrier molecule or biotin immobilised in an ELISA, where the bond of serum antibodies from humans is specifically detected, quantified and thus, assessed in their specificity by means of anti-human-IgG or anti-human-IgM according to a detection method known as such. Such a method is used, for example, to determine the natural antibody titre of MUC1-specific antibodies in the serum and, at the same time, to subdivide it into the different specificities. This is suitable, for example, for the tumour prognosis of breast cancer. Female patients with a high titre of antibodies against the MUC1 tumour epitope according to the invention have clearly improved prospects compared to patients with a lower titre against the MUC1 tumour epitope according to the invention.

The definitions of the terms introduced above can be applied mutatis mutandis for the terms in the embodiments described below.

Furthermore, the present invention relates to the use of a MUC1 molecule, a cell, a cell lysate or an antibody obtainable by means of a method according to the invention for the production of a pharmaceutical composition for the prevention or treatment of tumours.

Preferably, within the meaning of the use according to the invention, the pharmaceutical composition is a vaccine.

From the explanation given above it follows that the present invention further relates to the use of an antibody obtainable by means of a method according to the invention for the production of a diagnostic means for the diagnosis of tumours.

Finally, the present invention comprises a purified tumour-associated MUC1 molecule having an immunostimulatory effect in humans and, thus, obtainable by means of a method according to the invention.

The term "purified" defines a MUC1 molecule which can be produced by means of the method according to the invention. Thus, a purified tumour-associated MUC1 molecule also comprises a group of specific MUC1 glycoproteins which are characterised by the fact that they are able to trigger an immune response in humans, however, have only little or preferably no immunosuppressive effect. Further functional and structural characteristics of the purified MUC1 molecule according to the invention are also described in the examples below.

BRIEF DESCRIPTION OF THE DRAWINGS

1) GD-1: Antibodies binding to the PDTR (SEQ ID NO:3) motif only after the glycosylation thereof (GD refers to glycosylation-dependent). Example: A76-A/C7 (FIG. 1A). FIG. 1A also discloses "PDTRP" as SEQ ID NO: 10.

Figure 1A:
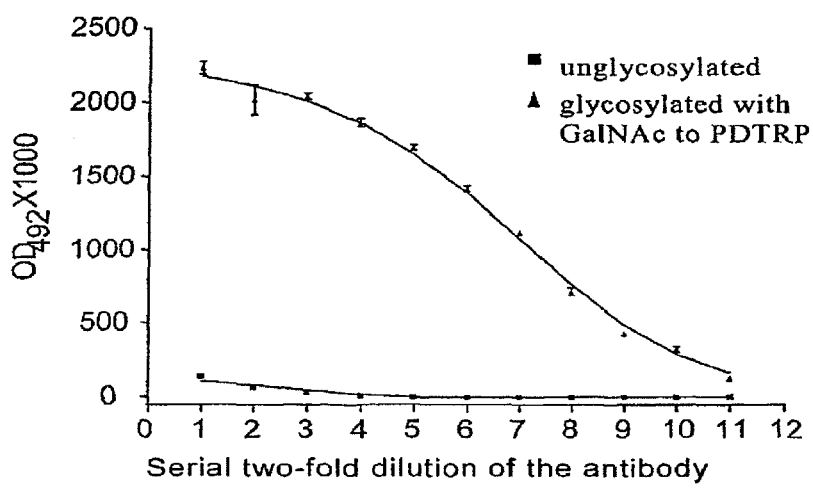
FIG. 1A-B shows examples for the binding behaviour of different anti-MUC1 antibodies. In total, 4 behaviour patterns were defined.
Figure 1B:
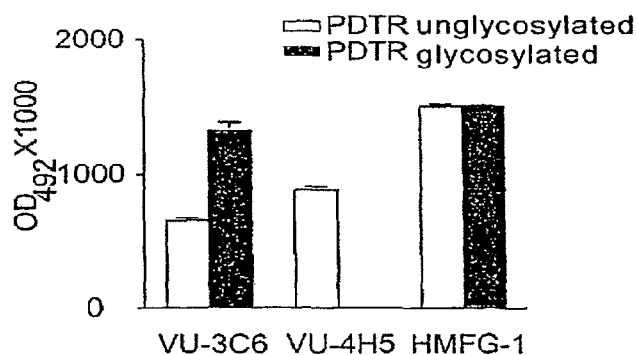

2) GD-2: Antibodies whose linkage is improved by glycosylation at the PDTR (SEQ ID NO:3) motif. Example: VU-3D1 (FIG. 1B).

3) iGD: Antibodies whose linkage is reduced or prevented (inverse glycosylation-dependency). Example: VU-4H5 (FIG. 1B).

4) GI: Antibodies whose linkage to the PDTR (SEQ ID NO:3) region is independent from the glycosylation thereof (glycosylation-independent). Example: HmFG-1 (FIG. 1B).

Figure 2:
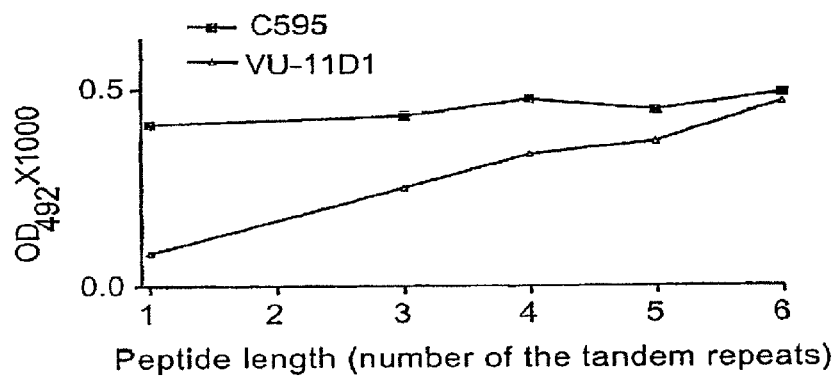

FIG. 2 shows examples for the binding behaviour of anti-MUC1 antibodies towards non-glycosylated MUC1 peptides of different lengths (1-6 tandem repeats).

The results show that antibodies which were produced by an immunisation of mice with tumour material
- positively depend on the glycosylation in the PDTR (SEQ ID NO:3) region of short MUC1 peptides (GD-1 and GD-2)

and
- positively depend on the increasing length of non-glycosylated MUC1 peptides and, thus, on the number of tandem repeats;
  - antibodies which were produced by an immunisation of mice with non-tumour material are
  - independent from (GI) or negatively dependent on (inversely dependent; iGD) the glycosylation in the PDTR (SEQ ID NO:3) region of short MUC1 peptides (GI)

or
- independent from the length of the MUC1 peptides and, thus, the number of tandem repeats.

Figure 3A:
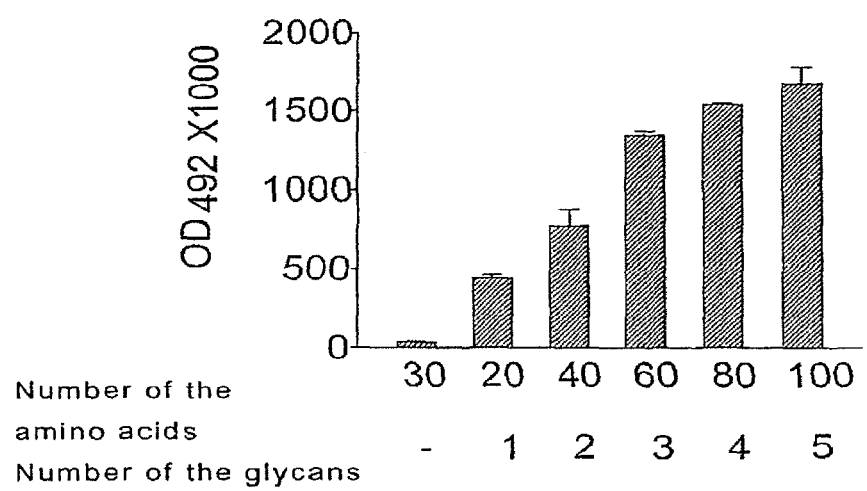

FIG. 3A shows an example of the binding of MUC1-specific monoclonal antibody (mab A76-A/C7) to glycosylated MUC1 peptides of different lengths (=different number of tandem repeats). FIG. 3A discloses "PDTR" as SEQ ID NO: 3.

Figure 3B:
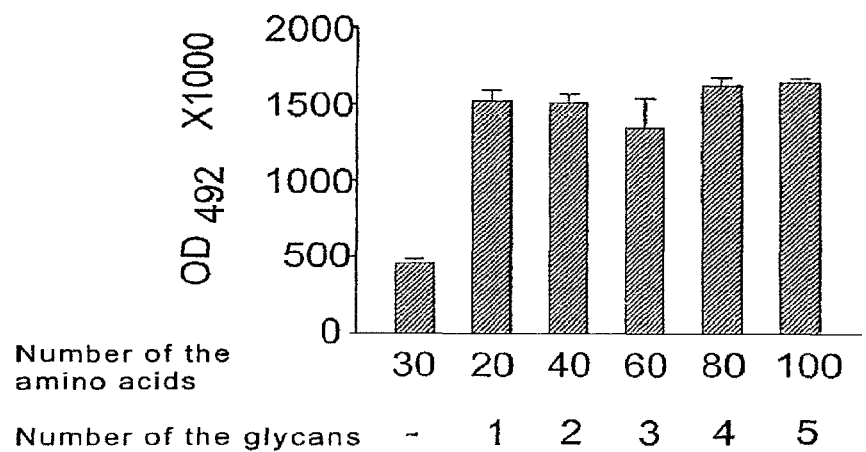

FIG. 3B shows an example of the binding of MUC1-specific monoclonal antibody (mab Mc5) to glycosylated MUC1 peptides of different lengths (=different number of tandem repeats). FIG. 3B discloses "PDTR" as SEQ ID NO: 3.

Figure 4:
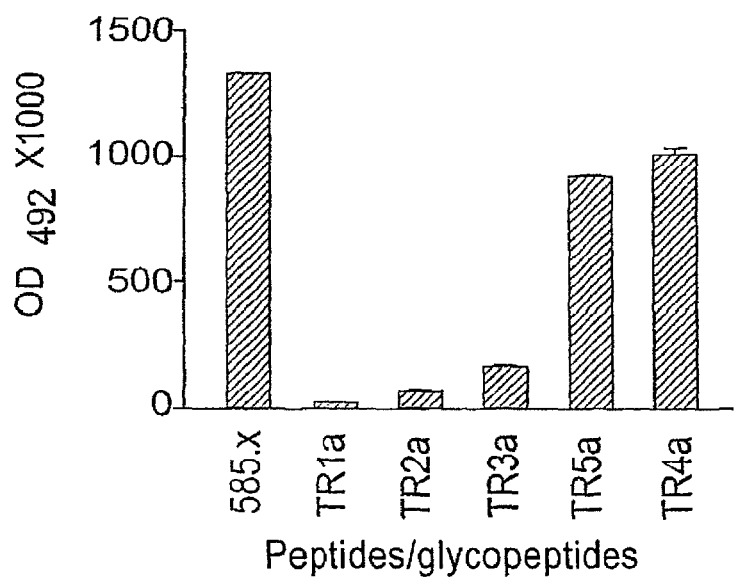

FIG. 4 shows the binding of the antibody VU-4H5 to glycosylated MUC1 peptides of different lengths. FIG. 4 discloses "PDTR" as SEQ ID NO: 3.

Figure 5A:
Figure 5A:
Figure 5:
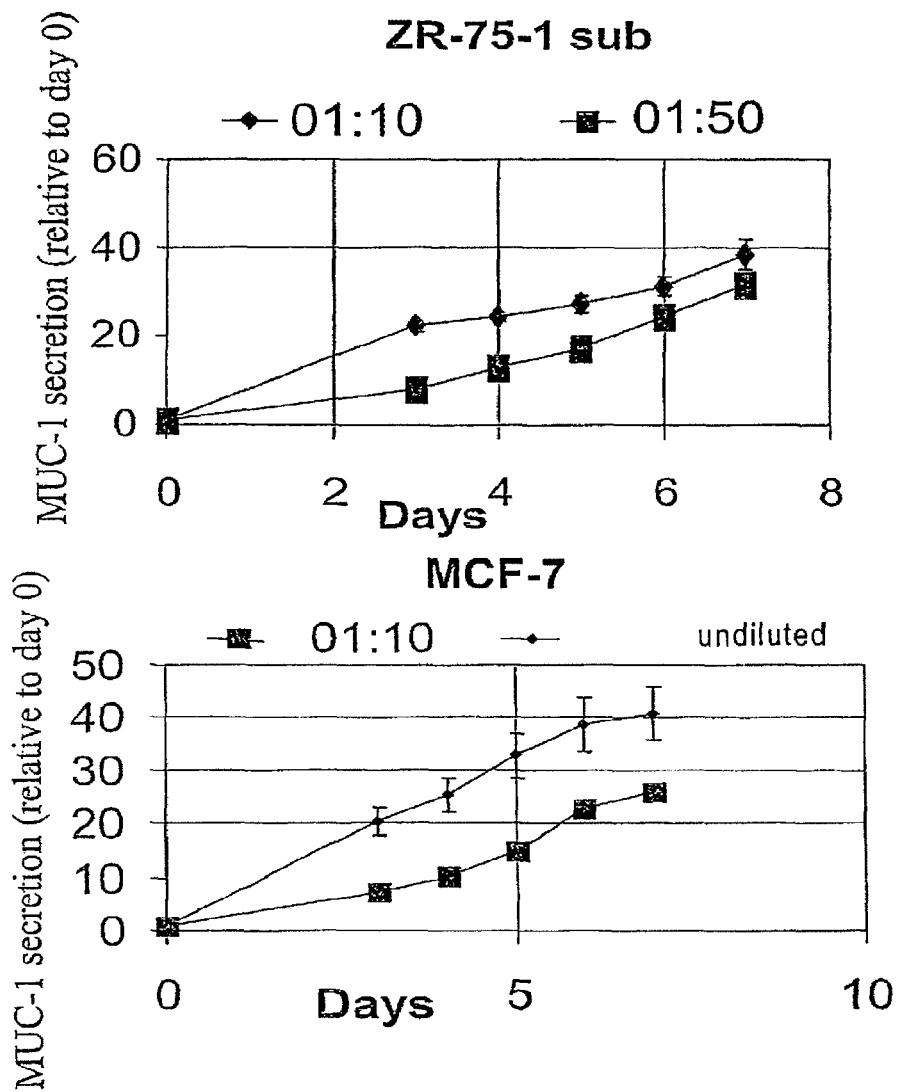

FIG. 5A: Immunocytochemical staining of ZR-75-1 cells (1) and cells of the subcell line (2) with the antibody A76-A/C7.

FIG. 5B: Secretion of A76-A/C7 positive MUC1 from ZR-75-1 sub and MCF-7 cells. The secreted MUC1 was detected 3, 4, 5, 6 and 7 days after spreading $10^5$ cells in the cell culture supernatant by means of ELISA with the HMFG1 and A76-A/C7 antibodies. Attention has to be paid to the different dilutions of the cell culture supernatants.

FIG. 5C: Expression vector for the integration of the MUC1 cDNA (SEQ ID NO: 1) (complementary sequence, SEQ ID NO: 11) under the control of the CMV promoter in the ZR-75-1 genome as well as the MUC1 cDNA sequence.

FIG. 5D: Rec site vector for the integration of the recombination site in the ZR-75-1 genome and illustration of the method of the integration.

Figure 5E:
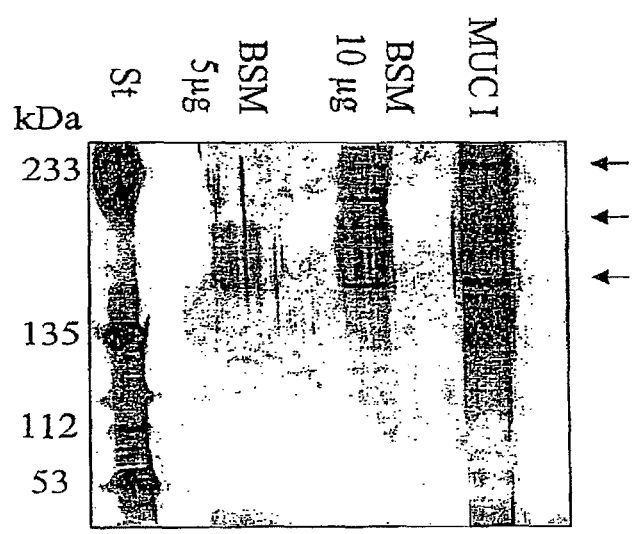

FIG. 5E: SDS-polyacrylamide gel analysis of different MUC1 preparations.

Figure 5F:
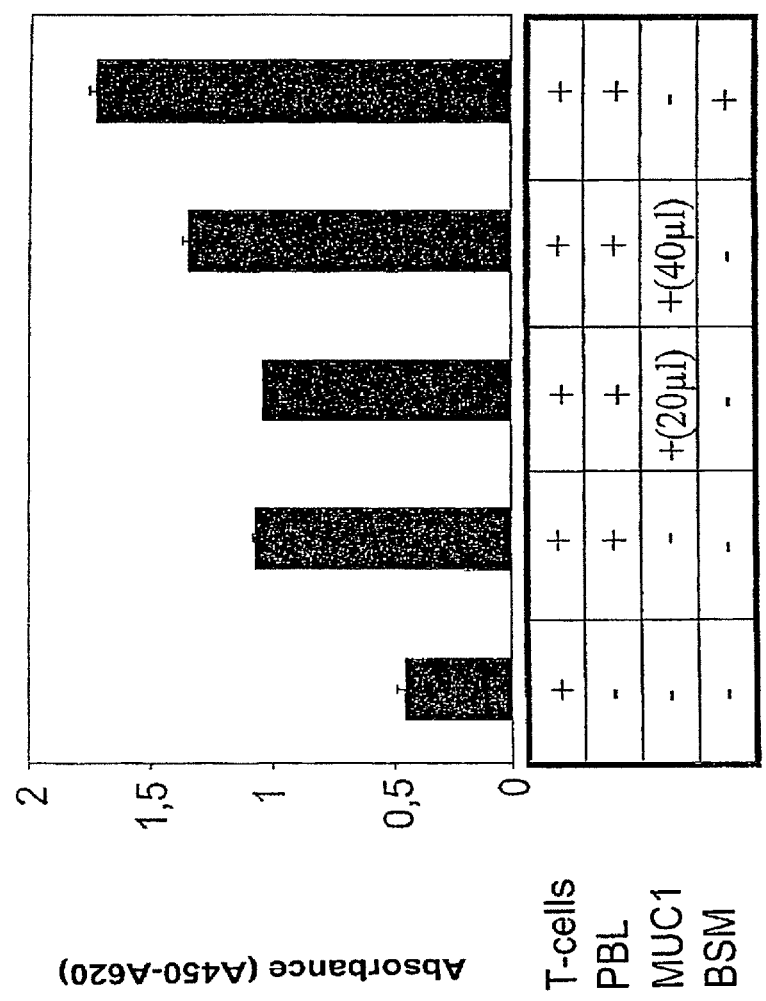

FIG. 5F: The purified secreted tumour-associated MUC1 show no immunosuppressive effects on T-cells in vitro.

Figure 6:
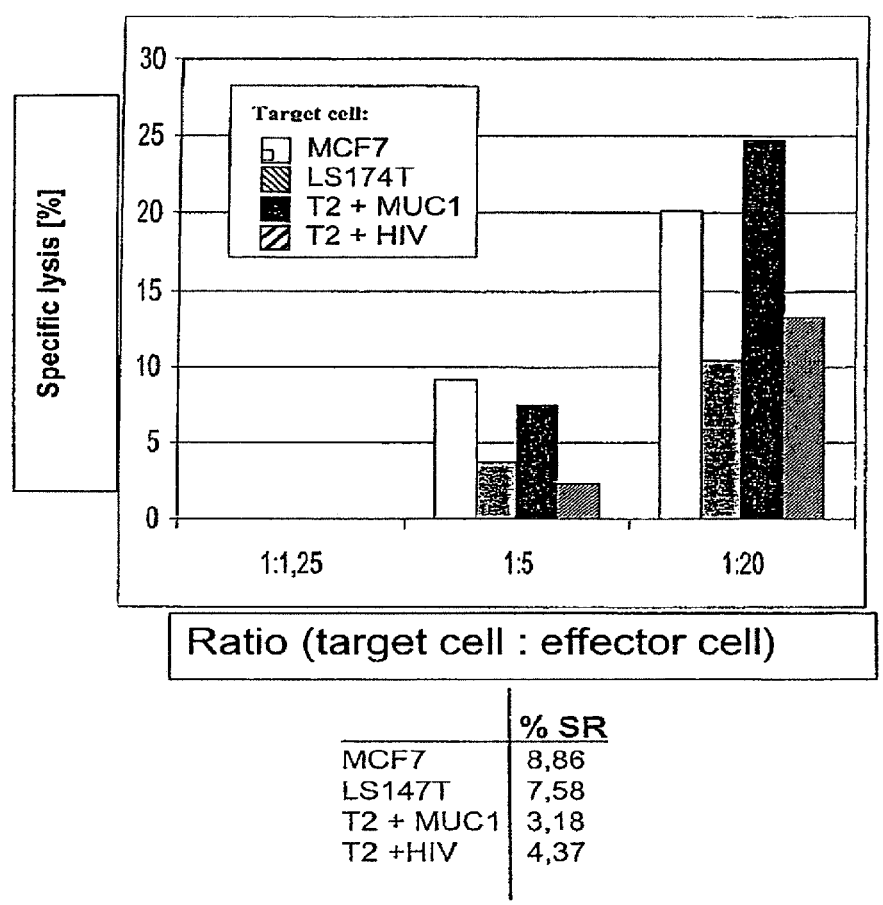

FIG. 6: Stimulation of naïve T-cells by means of the effective dendritic cells charged with the MUC1 of the invention and their MUC1-specific anti-tumour activity (details see exemplary text).

The invention is now illustrated by the following examples. The examples only serve the purpose of explanation and do not limit the scope of protection of the invention.

EXAMPLE 1

Binding Behaviour of Different Anti-MUC1 Antibodies to a MUC1 Peptide Dependent on the Glycosylation of the PDTR (SEQ ID NO:3) Motif Monoclonal anti-MUC1 antibodies (mouse) were tested in the enzyme immunoassay (ELISA) as to their binding capability towards synthetic MUC1 peptides and glycopeptides with the following sequence: biotin-APPAHGVT-SAPDT(GalNAc)RPAPGSTAPPAHGVYSA (SEQ ID NO:5). The same but non-glycosylated peptide served as control. The antigens were immobilised on streptavidin-coated microtestplates (BioTeZ, Berlin) at a concentration of 0.5 µg/ml (100 µl/well). After washing them three times with PBS/0.05% TWEEN20, various purified anti-MUC1 antibodies were applied in dilution series and incubated at 37° C. for 2 hours. Rabbit-anti-mouse-Ig, peroxidase-marked (Dako, Hamburg), served as the second antibody in a dilution of 1:4,000 (1.5 hrs, 37° C.). After washing it three times, the plate was developed with ortho-phenylenediamine and the colour reaction was stopped with 2.5 N sulfuric acid. The optical density was measured at 492 nm.

FIG. 1 shows examples for the binding behaviour of different anti-MUC1 antibodies. In total, 4 behaviour patterns were observed:

1) GD-1: Antibodies binding to the PDTR (SEQ ID NO:3) motif only after the glycosylation thereof (GD refers to glycosylation-dependent). Example: A76-A/C7 (FIG. 1A).

2) GD-2: Antibodies whose linkage is improved by glycosylation at the PDTR (SEQ ID NO:3) motif. Example: VU-3D1 (FIG. 1B).

3) iGD: Antibodies whose linkage is reduced or prevented by glycosylation at the PDTR (SEQ ID NO:3) motif (inverse glycosylation-dependency). Example: VU-4H5 (FIG. 1B).

4) GI: Antibodies whose linkage to the PDTR (SEQ ID NO:3) region is independent from the glycosylation thereof (glycosylation-independent). Example: HMFG-1 (FIG. 1B).

Table 1 contains an overview of the binding patterns of a panel of monoclonal anti-PDTR (SEQ ID NO:3) (MUC1) antibodies with PDTR (SEQ ID NO:3)-glycosylated and non-glycosylated MUC1 peptides. The table is divided in two sub-tables (A) and (B). Table 1A contains antibodies which were produced by an immunisation with MUC1 from tumour material. Table 1B contains antibodies which were produced by an immunisation with MUC1 from non-tumour material.

TABLE 1

Antibodies against the immunodominant PDTR (SEQ ID NO: 3) region of the MUC1: Binding behaviour towards MUC1 peptides glycosylated at the PDTR (SEQ ID NO: 3) and non-glycosylated dependent on the type of the immunogen

A. MUC1 from tumour material

| Antibody | Immunogen | binding pattern | | | |
|---|---|---|---|---|---|
| | | GD-1 | GD-2 | iGD | GI |
| A76-A/C7 | tumour cell line T-47D | + | | | |
| VU-11E2 | tumour cell line ZR75-1 | + | | | |
| VU-11D1 | tumour cell line ZR75-1 | + | | | |
| Ma552 | tumour cell line ZR75-1 | | + | | |
| VU-3C6 | tumour cell line ZR75-1 | | + | | |
| BC4E549 | membrane preparation of the tumour cell line T-47D | | + | | |
| VU-12E1 | tumour cell line ZR75-1 | | + | | |
| VU-3D1 | tumour cell line ZR75-1 | | + | | |
| b-12 | mixture of several tumour cell lines | | + | | |
| B27.29 | MUC1 from tumour Ascites | | + | | |
| MF 06 | MUC1 from ovarian cyst | | + | | |

B. MUC1 peptides (non-glycosylated) or preparations from non-tumour material

| Antibody | immunogen | binding pattern | | | |
|---|---|---|---|---|---|
| | | GD-1 | GD-2 | iGD | GI |
| VU-4H5 | 60-mer, BSA conjugated | | | + | |
| HMPV | HMFG from breast milk | | | + | |
| HMFG-1 | HMFG from breast milk | | | | + |
| BC2 | HMFG from breast milk | | | | + |
| VA2 | 100-mer fusion protein | | | | + |
| Mc5 | HMFG from breast milk | | | | + |
| E29 | HMFG from breast milk | | | | + |
| BC3 | HMFG from breast milk | | | | + |
| 214D4 | MUC1 peptide (fusion protein) | | | | + |
| BCP8 | MUC1 peptide | | | | + |
| VA1 | 100-mer fusion protein | | | | + |
| C595 | MUC1 from urine | | | | + |
| BC4W154 | HMFG from breast milk | | + | | |

EXAMPLE 2

Binding of MUC1-Specific Antibodies Towards the Immunodominant PDTR (SEQ ID NO:3) Region to Non-Glycosylated MUC1 Peptides of Different Lengths (Non-Glycosylated Multiple Tandem Repeats)

The MUC1 peptides of the following sequence of different lengths (oligomerisation)

```
                                ((SEQ ID NO: 6)_n)
[VTSAPDTRPAPGSTAPPAHG]_n;
n = 1-6
``` were immobilised by drying on a 96-well-TC-microtitre plate at a concentration of 0.5 μg/well in coating buffer at 37° C. overnight. The plates were washed (PBS/0.05% TWEEN20) and subsequently incubated with 50 μl/well purified antibodies at a concentration of 10 μg/ml for 2 hrs. After washing the plate three times, it was incubated with peroxidase-marked polyclonal rabbit-anti-mouse immunoglobulin serum (P260, Dako) in a dilution of 1:2,000. After washing the plate three times, it was developed with ortho-phenylenediamine and the colour reaction was stopped with 2.5 N sulfuric acid. The optical density was measured at 492 nm.

The number of tandem repeats per solution was kept constant in the experiments by using, per well, the same amounts in weight for all the peptides compared.

The results are summarised in Table 2.

The classification was carried out according to the ratio of the optical density 100-mer/20-mer=X as follows:

Without significant bond to the 20-mer, however, a clearer bond to the 100-mer: group LD1 (absolutely dependent on length)

X>3.0: group LD2 (strongly dependent on length)

X=1.5-3.0: group LD3 (moderately dependent on length)

X<1.5: group LI (independent from length).

Furthermore, the data about the glycosylation dependency from Table 1 have been included in the table for comparison.

TABLE 2

Binding behaviour of monoclonal anti-MUC1 antibodies against the immunodominant PDTR (SEQ ID NO: 3) motif: Binding behaviour towards MUC1 peptides glycosylated at the PDTR (SEQ ID NO: 3) and non-glycosylated, dependent on the type of the immunogen and with non-glycosylated MUC1 peptides of different lengths (1-6 tandem repeats). Binding behaviour of the antibodies dependent on:

| | glycosylation | | | | length | | | |
|---|---|---|---|---|---|---|---|---|
| | GD-1 | GD-2 | iGD | GI | LD-1 | LD-2 | LD-3 | LI |

A. MUC1 from tumour material

| | | | | | | | | |
|---|---|---|---|---|---|---|---|---|
| A76-A/C7 | + | | | | | + | | |
| VU-11E2 | + | | | | | + | | |
| VU-11D1 | + | | | | | + | | |
| Ma552 | | + | | | | + | | |
| VU-3C6 | | + | | | | + | | |
| BC4E549 | | + | | | | | + | |
| VU-12E1 | | + | | | | | + | |
| VU-3D1 | | + | | | | | | + |
| b-12 | | + | | | | | | + |
| B27.29 | | + | | | | | | + |
| MF 06 | | + | | | | | | + |

B. MUC1 peptides (non-glycosylated) or preparations from non-tumour material

| | | | | | | | | |
|---|---|---|---|---|---|---|---|---|
| VU-4H5 | | | + | | | + | | |
| HMPV | | | + | | | + | | |
| HMFG-1 | | | | + | | + | | |
| BC2 | | | | + | | + | | |
| VA2 | | | | + | | + | | |
| Mc5 | | | | + | | + | | |
| E29 | | | | + | | | + | |
| BC3 | | | | + | | | + | |
| 214D4 | | | | + | | | + | |
| BCP8 | | | | + | | | + | |
| VA1 | | | | + | | | + | |
| C595 | | | | + | | | | + |
| BC4W154 | | + | | | | | | + |

FIG. 2 shows examples for binding behaviour of anti-MUC1 antibodies towards non-glycosylated MUC1 peptides of different lengths (1-6 tandem repeats).

EXAMPLE 3

Binding of MUC1-Specific Antibodies to Multiple Tandem Repeats Glycosylated to PDTR (SEQ ID NO:3)

Synthetic MUC1 glycopeptides of the type:

((SEQ ID NO:_7)$_n$)
[AHGVTSAPDT(GalNAc)RPAPGSTAPPA]$_n$;
n = 1-5 were immobilised by drying on a 96-well-TC-microtestplate at a concentration of 0.5 μg/well in water at 4° C. overnight. The plates were washed (PBS with 0.05% TWEEN20) and subsequently incubated with 50 μl/well of a solution of 10 μg/ml purified antibody in PBS/BSA at 37° C. for 2 hrs. After washing the plate three times, it was incubated with peroxidase-marked polyclonal rabbit-anti-mouse immunoglobulin serum (Dako) in a dilution of 1:2,000 at 37° C. for 1.5 hrs. After washing the plate three times, it was developed with ortho-phenylenediamine and the colour reaction was stopped with 2.5 N sulfuric acid. The optical density was measured at 492 nm.

The number of tandem repeats per solution was kept constant in the experiments by using the same amounts in weight for all the glycopeptides compared per well.

FIG. 3 shows 2 examples for the linkage of MUC1-specific monoclonal antibodies to glycosylated MUC1 peptides of different lengths (=different number of tandem repeats).

TABLE 3

Binding behaviour of monoclonal anti-MUC1 antibodies towards the immunodominant PDTR (SEQ ID NO: 3) motif: Binding behaviour towards MUC1 peptides glycosylated at the PDTR (SEQ ID NO: 3) and non-glycosylated MUC1 peptides of different lengths (1-6 tandem repeats) dependent on the type of immunogen.

Binding behaviour of the antibodies dependent on:

| | glycosylation | | | length | | | | Length with glyco-sylation |
|---|---|---|---|---|---|---|---|---|
| | GD-1 | GD-2 | iGD | GI | LD-1 | LD-2 | LD-3 | LI | |
| A. Immunogen: MUC1 from tumour material |
| A76-A/C7 | + | | | | + | | | | + |
| VU-11E2 | + | | | | + | | | | + |
| VU-11D1 | + | | | | + | | | | (+) |
| Ma552 | | + | | | + | | | | − |
| VU-3C6 | + | | | | + | | | | − |
| BC4E549 | + | | | | | + | | | (+) |
| VU-12E1 | + | | | | | + | | | (+) |
| VU-3D1 | + | | | | | | + | | (+) |
| b-12 | + | | | | | | + | | (+) |
| B27.29 | + | | | | | | + | | − |
| MF 06 | + | | | | | | + | | − |
| B. Immunogen: MUC1 peptide (non-glycosylated) or preparations from non-tumour material |
| VU-4H5 | | | + | | | + | | | + |
| HMPV | | | + | | | + | | | (+) |
| HMFG-1 | | + | | | | + | | | − |
| BC2 | | | | | | + | | | − |
| VA2 | | | | | | + | | | − |
| Mc5 | | | | | | + | | | − |
| E29 | | | | | | | + | | − |
| BC3 | | | | | | | + | | − |
| 214D4 | | | | | | | + | | − |
| BCP8 | | | | | | | + | | − |
| VA1 | | + | | | | + | | | − |
| C595 | | + | | | | | + | | − |
| BC4W154 | + | | | | | | + | | (+) |

The results show that most antibodies which were produced by an immunisation from mice with tumour material are positively dependent on the increasing length of PDTR (SEQ ID NO:3)-glycosylated MUC1 glycopeptides. This corresponds to an additive effect of the antibodies with regard to the PDTR (SEQ ID NO:3) glycosylation and the length with multiple tandem repeats. A subgroup (A76-A/C7, VU-11E2, VU-11 D1) shows a particularly strong additive effect in that the linkage of the antibodies to the MUC1 glycopeptides with several PDTR (SEQ ID NO:3)-glycosylated tandem repeats is clearly increased up to many times over (see FIG. 3A) in comparison with the linkage to short PDTR (SEQ ID NO:3)-glycosylated MUC1 glycopeptides (as in example 1) as well as in comparison with the linkage to non-glycosylated MUC1 peptides with several tandem repeats (as in example 2). Antibodies with an additive binding effect exhibit a particularly high affinity towards natural tumour MUC1 consisting of multiple tandem repeats.

As a rule, the antibodies which were produced by an immunisation of mice with non-tumour material and which are PDTR (SEQ ID NO:3) glycosylation-independent show no additive effect, not even when the bonds are dependent on length with regard to non-glycosylated MUC1 peptides (LD-3 and LD-2).

FIG. 3B shows an example of an antibody bond without additive effect.

Antibodies VU-4H5 and HMPV which show an iGD linkage show an additive effect described in detail in example 4 as a special case.

EXAMPLE 3

Binding of MUC1-Specific Antibodies of the GID Group to Glycopeptides Glycosylated to PDTR (SEQ ID NO:3) with Tandem Repeats The method is the same as the one described under example 3.

The results show that the linkage of the VU-4H5 antibody from the GID group depends on the number of the tandem repeats per MUC1 glycopeptide. This result is surprising since this antibody practically does not bind to short DTR-glycosylated MUC1 peptides. However, it increasingly binds better to DTRP (SEQ ID NO:8)-glycosylated MUC1 glycopeptides with increasing number of tandem repeats. This antibody shows a similar additive effect as the one described in example 3 and, thus, takes an intermediate position, which can also be used for various applications within the meaning of the invention.

FIG. 4 shows the linkage of the VU-4H5 antibody to glycosylated MUC1 peptides with different numbers of tandem repeats.

EXAMPLE 5A

Production of Immunostimulatory MUC1 Carrying the MUC1 Tumour Epitope for Vaccination a) Identification of Human Cells Strongly Expressing the MUC1 with the Tumour Epitope ZR-75-1 cells (ATCC:CRL 1500) were cultivated in RPMI medium with 10% FKS and 1% glutamine at 37° C., 8% $CO_2$ and 95% humidity of atmosphere. Compared to other cell lines, these cells already express large amounts of the protein with the tumour epitope on the cell surface. FIG. 5A shows immunocytochemical colouring of the ZR-75-1 cells with the A76-A/C7 antibody. The immunocytochemical colouring was carried out by dripping cells on an object carrier, which were then immobilised by incubation in the cell culture incubator in a humid chamber for 30 min and, subsequently, on the object carrier at room temperature for 15 min. The cells were fixed in 5% formalin in PBS for 5 min. After washing the cells with PBS three times, they were incubated with the primary antibody at room temperature for 1.5 hrs, which was diluted in the form of a hybridoma culture supernatant 1:5. After washing the cells three times again with PBS, the secondary antibody (anti-mouse IgG from the rabbit coupled to Cy3, Dianova) was added in a dilution of 1:1000 and incubated for another 30 min at room temperature. After washing the cells three times again, the embedding took place in the Mowiol solution (Calbiochem, Heidelberg, Germany). The isotypic IgG antibody MOPC-21 (Sigma) was used as negative control. The immunocytochemical colouring of the ZR-75-1 cells with the A76-A/C7 made clear that the cell population was not homogenous with regard to the expression of the tumour epitope (FIG. 5A1). In order to increase the expression and to obtain a homogenous A76-A/C7 positive ZR-75-1 cell population, the A76-A/C7 positive ZR-75-1 cells were selected by magnetobeads and, subsequently, clones were cloned by limited dilution, which carry a particularly strong and homogenous expression of suitable MUC1 molecules. The selection took place by binding of $10^7$ cells and the A76-A/C7 antibody (50 µl of the hybridoma culture supernatant) and anti-IgM antibodies coupled to magnetobeads as well as MS columns from Miltenyi Biotec GmbH (Bergisch Gladbach, Germany) under standard conditions (MACS see product description as to MS columns). The selected cells were cloned by limited dilution in that the cells were adjusted on a cell titre of 150 to 300 cells per 15 ml culture medium. 100 µl of this dilution is distributed on a microtitre plate in such a way that 1-2 cells per well are cultivated. The distribution on the microtitre plate is checked in the microscope. In this manner, ZR-75-1 sublines could be isolated which express the tumour epitope homogenously and to a larger extent, as is shown in the immunocytochemical colouring in FIG. 5A2.

FIG. 5B shows that, in comparison with other cell lines (e.g., MCF-7), the MUC1 protein, too, is discharged into the cell culture medium in large amounts. This is the result from ELISA analyses with the HMFG-1 (clone 1.10.F3, Beckman/Coulter) as catcher antibody and the A76-A/C7 as detection antibody (FIG. 5B). The samples for this ELISA were obtained by sowing $10^5$ cells per ml cell culture medium, culturing them under standard conditions for 3 days (see above), subsequently taking an aliquot each day and separating the cell culture supernatant from the cell pellet by centrifugation. 50 µl of these supernatants were undiluted or used in the dilutions stated (FIG. 5B) in the ELISA. The HMFG-1-A76-A/C7 sandwich ELISA was carried out by coating microtitre plates with the catcher antibody HMFG-1, diluted 1:250 in PBS (no indications as to concentration by the manufacturer), in 50 µl PBS per well at 4° C. overnight. Subsequently, the coated plates were blocked twice with 0.1% TWEEN 20 in PBS at room temperature. The blocking buffer was removed and the plates were washed with washing buffer again three times so as to then put 50 µl of the samples, undiluted or with the cell culture medium in the dilutions stated, in each well and incubate it at room temperature for 1.5 hrs. The primary antibody was substituted by cell culture medium or 2% BSA, 0.1% TWEEN 20 in PBS as negative control. After washing it with washing buffer three times, the biotinylated, affinity-purified A76-A/C7 antibody was added in a 1:500 dilution and incubated at room temperature for another hour. After washing it three times again, the binding of streptavidin (1:500 undiluted) coupled to horseradish peroxidase took place at room temperature for 20 min. Finally, the plates were washed in washing buffer twice and in PBS once. The colouring reaction took place in 50 µl 50 mM acetate buffer pH 6.0 with 1 mg/ml TMB (3,3',5,5' tetramethylbenzidine, stock solution: 100 mg/ml in DMSO, Sigma) and 0.025% $H_2O_2$ (Sigma) in the dark at room temperature for 20 min. The colouring reaction was stopped by adding 25 µl 2.5 N sulfuric acid (final concentration 0.07 N) and measured in the ELISA reader at 450 nm with a reference filter of 620 nm.

The glycosylation of the secreted MUC was analysed in the ELISA by means of different antibodies. In this context, in comparison with the HMFG-1-A76-A/C7 sandwich ELISA described above, the A76-A/C7 antibody was exchanged for antibodies binding the tumour-associated carbohydrates Tn (HB-1, Dako, Glostrup, Denmark) or TF (A78-G/A7, U. Karsten et al, 1995) with high affinity. The detection of the secondary antibody (HB-1 and A78-G/A7) took place with an anti-mouse IgM (diluted 1:5,000) coupled to a POD. The colouring reaction was carried out in 25 mM citric acid, phosphate buffer pH 5.0 with 0.04% $H_2O_2$ and 0.4 mg/ml o-phenylenediamine (Sigma) in the dark at room temperature for 20 min, stopped by adding 2.5 N sulfuric acid (final concentration 0.07 N) and measured in the ELISA reader at 490 nm with a reference filter of 630 nm. It was possible to detect the tumour-associated carbohydrate epitope Tn and TF, the letter only after treatment with neuraminidase of the MUC1.

b) Overexpression of Secretory Tumour-Associated MUC1 Molecules

The overexpression of the secretory MUC1 was achieved by integration of the MUC1 cDNA, whose expression is under the control of a strong promoter (FIG. 5C), into a site in the genome of the ZR-75-1 cells which is particularly transcription-active. First, the cells were transfected with the recsite vector which, after integration of the recsite into the genome achieved by antibiotics selection, mediates a stable expression of the LacZ gene. The stably transfected cells were cloned by limited dilution (see next paragraph) and the cells showing the highest LacZ activity were identified. These cells allowed the integration of the MUC1 cDNA with the CMV promoter into a transcription-active site in the genome via the recsite (FIG. 5D). The MUC1 cDNA was amplified by means of RT-PCR from ZR-75-1 cells and cloned by restrictions into the expression vector.

Cloning of Cells by Limited Dilution

The cloning of cells by limited dilution is carried out by adjusting the cells on a cell titre of 150 to 300 cells per 15 ml culture medium. 100 μl of this dilution is spread on a microtitre plate in such a way that 1-2 cells per well are cultivated. This distribution on the microtitre plate is checked in the microscope.

c) Purification of the Secretory MUC1

The secretory MUC1 was purified from several liters cell culture supernatant by means of an A76-A/C7 affinity chromatography column under standard conditions. The analysis of the purified protein resulted in several bands in the SDS polyacrylamide gel, which co-migrated with a commercially available MUC1 preparation (FIG. 5E).

EXAMPLE 5B

Influence of the T-Cell Activation by Purified Secretory MUC1 Carrying the MUC1 Tumour Epitope By means of the secreted tumour-associated MUC1 purified with A76-A/C7, incubation was carried out with accumulated T-cells (see above) together with irradiated PBLs. T-cells and PBLs came from two different patients so that an allogene reaction was caused, which was detected by means of T-cell proliferation in BrdU-Assay (see above). In the presence of purified secreted tumour-associated MUC1, no indications were found as to an immunosuppressive effect of MUC1 in this mixed leukocyte reaction. On the contrary, a clear stimulatory effect could be observed at the higher concentration. Reference substances were PBS and 10 μg/ml bovine submaxillary mucine (BSM) respectively (FIG. 5F).

EXAMPLE 6

Production of a Monoclonal Antibody by Means of Immunostimulatory MUC1 Purified with A76-/C7, which Exhibits a Particularly Strong Additive Binding Effect 1. Origin of the Initial Cells a) The spleen cells were obtained under sterile conditions (Laminarbox) from a female mouse of the inbred strain Balb/c, which was immunised according to 2.

b) X63-Ag8.653 (plasmacytoma cell line of Balb/c; Kearney et al., J. Immunol. 123:1548-1550, 1979) was used as fusion cell line. Maintenance took place in medium RPMI 1640 while adding 10% inactivated foetal calf serum and $5 \times 10^{-5}$ M β-mercaptoethanol.

c) Peritoneal cells from Balb/c mice of the same origin as under a) served as feeder cells. They were taken the day before the fusion experiment and/or the cloning under sterile conditions according to a published method and sown into cell culture microtitre plates (Karsten, in: Friemel, Immunologische Arbeitsmethoden, $4^{th}$ edition, Jena 1991, pp. 309-320).

2. Immunisation

100 μg MUC1 served as immunogen, which was obtained by means of affinity chromatography with A76-A/C7 (see example 5). MUC1 was applied in PBS with incomplete Freund's adjuvant i.p. and boosted with MUC1 purified with A76-A/C7 5 and 9 weeks later, respectively.

3. Generation of the Hybridomas

The hybridoma technique was carried out according to published standard methods (Peters et al., Monoklonale Antikörper, Herstellung and Charakterisierung, Berlin, 1985). The fusion took place 4 days after the last booster. PEG was used as fusogenic agent. The selection of the hybridomas took place by means of azaserine/hypoxanthine; mouse peritoneal cells were used for support of growth.

The forming hybridomas were tested by means of ELISA with immobilised MUC1, MUC1 glycopeptides and in immunofluorescence tests with MUC1 positive cell lines (for example T-47D-cells, ZR-75-1 cells and subcell lines) on the secretion of specific antibodies.

Cloning took place by means of limiting dilution according to standard techniques in the presence of mouse peritoneal cells (Karsten, in: Friemel, Immunologische Arbeitsmethoden, $4^{th}$ edition, Jena 1991, pp. 309-320). The isotypes were detected by means of a commercial isotypes-ELISA-kit (Pharmigen).

EXAMPLE 7

Tests as to the Tumour-Specific Cytotoxicity a) Identification and Generation of a Subpopulation of Human MCF-7 Cells which Strongly Express MUC1 with the Tumour Epitope MCF-7 cells (ATCC:HTB-22) were—as described in detail under example 5 for ZR-75-1-cultivated and isolated from the cells by means of magnetobeads with A76-A/C7 cells and, subsequently, clones carrying a particularly strong and homogenous expression of suitable MUC1 molecules were cloned by limited dilution. In this way, MCF-7 sublines could be isolated, which expressed the tumour epitope in a homogenously and stronger than the initial line.

b) Generation of Mature Nemod-mDC Cells Charged with Lysates from MCF-7

As to dendritic cells, effective dendritic cells (DE 10139428.4) from NemodDC-1 cells stemming from MUTZ-3 were produced. Effective dendritic cells were differentiated by differentiation from NemodDC-1 cells (precursor cells, prec-NemodDC) to immature dendritic cells (i-NemodDC), charged with antigen and, subsequently, matured to mature effective dendritic cells (m-NemodDC) which are able to activate T-cells in an antigen-specific way. I-NemodDC which are charged with antigens absorb these cells, process them and present peptide fragments of the antigens in the context of their MHC class molecules, for example MHC I-A2. By means of these effective dendritic cells, both specific CTL- and helper T-cells from naïve T-cells can be stimulated and NKT-cells can be stimulated and expanded.

$4 \times 10^6$ prec-Nemod-DC cells were differentiated in 40 ml reaction volume in aMEM+20% FCS+10% CM5637 with 1,000 U/ml GM-CSF, 1,000 U/ml IL-4 and 2.5 ng/ml TNFα for 7 days. Subsequently, the cells (I-NemodDC) were charged with a suitable amount of tumour cell lysate from the MCF-7-cells described above—which were produced by alternating freezing and thawing by means of liquid nitrogen—for 6 hrs and, subsequently, matured with TNFα for another 24 hrs, irradiated (30 Gy) and used for stimulation of T-lymphocytes.

c) Isolation of CD8+-T-Cells by Means of Microbeads

CD8+-T-cells cells HLA-A2 from positive donors were purified via a MAC isolation by means of magnetbeads coated with antibodies (Miltenyi, manufacturer's instructions) according to known methods from PBMC from usual buffy coat preparations.

d) Generation of Cytotoxic T-Cells (CTLs)

The CD8+-T-lymphocytes ($1 \times 10^6$ CD8+-T-lymphocytes/ml) of a HLA-A2 positive donor were stimulated weekly with m-NemodDC (ratio 1:10) charged with tumour cell lysate (MCF7 lysates) in medium (AIM V+10 U/ml IL-2 from day 7) (prime+restimulation).

e) Cytotoxicity Test

First, the target cells (MCF-7, LS 174 T and T2) which are in a physiologically stable and vital state are washed in cold medium (DMEM+5% FCS) and, after centrifugation (300×g, 7 min, RT) added to europium buffer (50 mM HEPES, 93 mM sodium chloride, 5 mM potassium chloride, 2 mM magnesium chloride, 10 mM DTPA, 2 mM europium-Ill-acetate). During this process, $5 \times 10^6$ target cells with a volume of 800 µl were transferred into an electroporation cuvette (d=4 mm). Before and after the electroporation, an incubation period of 6 to 10 min on ice took place. The electroporation was carried out with an Eppendorf Multiporator (30 µs, 710 V or 1,100 V and 1 puls). After washing the cells with medium five times, the marked target cell is ready for use in the cytotoxicity test. For this purpose, it was either used directly after the determination of the vitality and cell density (MCF-7 or LS 174 T) or marked with peptide (MUC1 A2 peptide: e.g., LLLLTVLTL (SEQ ID NO:9); irrelevant HIV-gag A2 peptide; 5 µg/ml each) (T2 cells) for another 2 hours so as to analyse peptide-specific effector cells. For the cytotoxicity test, marked target cells (5 to $10 \times 10^3$) were presented in a volume of 100 µl/well in a microtitre plate with an arch. Subsequently, effector cells, also in a volume of 100 µl, were added at different cell concentrations so that the result of the ratio of effector cell and target cell was 1.25:1 to 100:1. Apart from these solutions, samples were prepared for the determination of the background signal (BR) of the spontaneous and maximum release. The background signal was a cell-free medium sample at the beginning of the experiment. The spontaneous release (SR) allows assessment of the stability of the marking of the target cell with europium. For the determination, marked target cells were cultivated without effector cells and, after the end of the incubation period, the concentration of the released europium was determined. The maximal release (MR) was determined by means of marked target cells which were incubated, also without effector cells but with an artificial reagent (here with 50% of the purest ethanol), for the testing period and brought to total lysis. According to the amounts defined above, the percentage of the spontaneous release was calculated, which, for the assessment of a successful test, should be below 30%.

Furthermore, the percentage of the specific, cytotoxic activity of the effector cell was characterised.

$$\% \text{ spontaneous release} = \frac{SR(\text{counts}) - BR(\text{counts})}{MR(\text{counts}) - BR(\text{counts})} \times 100$$

$$\% \text{ specific release} = \frac{\text{effector/target cell(counts)} - SR(\text{counts})}{MR(\text{counts}) - SR(\text{counts})} \times 100$$

After the incubation period of 4 hours, the culture supernatant containing the europium was separated by means of centrifugation of the microtitre plate (500×g, 5 min, RT). Subsequently, 20 µl of this culture supernatant were transferred to a presented microtitre plate with a flat bottom with 200 µl enhancement solution/well and incubated on a plate shaker for another 15 min. During this incubation period, a fluorescent complex results from the europium DTPA chelate under formation of a europium-NTA chelate. The samples were measured in a time-delayed fluorometer (Victor$^2$, PerkinElmer) at a wave length of 613 nm.

In the experiment, MCF-7 was used as relevant target cell (FIG. 6, MCF7) and LS 174 T (FIG. 6, LS 174T) was used as irrelevant target cell. Furthermore, T2 cells which were not able to process and which can only be charged on their MHC class I A2 molecules by defined A2 peptides were used. In this context, a MUC1-A2-peptide was used for testing an effective stimulation of originally naïve T-cells which are specifically directed against MUC1 by means of the MUC1 molecules of the invention, which, in the present example, are present in the corresponding cell lysates (T2+MUC1). An irrelevant HIV gag A2 peptide was used as negative control (T2+HIV).

The data show that by means of the MUC1 molecules of the invention in a cell lysate a MUC1-specific cytotoxic immune response can be achieved against cells carrying MUC1 on the surface in the context of HLA-A2. These immunological data show that the MUC1 molecules of the invention can be used both as such for the activation of an effective anti-tumour response as well as in form of dendritic cells which were charged with the MUC1 molecules of the invention. Moreover, the data show that MUC1-specific T-cells can be ex vivo expanded and specifically activated by means of the MUC1 molecules and dendritic cells of the invention, which demonstrates a suitability for adoptive T-cell therapies.

We claim the following:

1. A pharmaceutically acceptable composition comprising isolated glycosylated MUC1 molecules secreted by a ZR-75-1 cell and one or more adjuvants selected from QS-21, GPI-0100, saponins, montanide adjuvants, Detox, bacterial adjuvants, BCG, and incomplete Freund's adjuvant, wherein the glycosylated MUC1 molecules comprise glycosylated PDTR (SEQ ID NO:3) regions recognized by an A76-A/C7 antibody, and are able to generate a stimulatory immune response to MUC1-positive tumor cells in vitro.

2. A pharmaceutically acceptable composition comprising isolated glycosylated MUC1 molecules secreted by a ZR-75-1 cell and one or more adjuvants, wherein the glycosylated MUC1 molecules comprise glycosylated PDTR (SEQ ID NO:3) regions recognized by an A76-A/C7 antibody, and are able to generate a stimulatory immune response to MUC1-positive tumor cells in vitro, and wherein the glycosylated MUC1 molecules are obtained by:

a) contacting a mixture of MUC1 molecules from a cell culture supernatant of the ZR-75-1 cell with an A76-A/C7 antibody for a period of time which is sufficient and under conditions which are suitable so that an immune complex is formed;

b) isolating the immune complex; and c) separating the glycosylated MUC1 molecules having glycosylated PDTR (SEQ ID NO:3) regions from the immune complex.

3. The pharmaceutically acceptable composition of claim 2, wherein the mixture of MUC1 molecules is contacted with an A76-A/C7 antibody affinity chromatography column.

4. A pharmaceutically acceptable composition comprising isolated glycosylated MUC1 molecules secreted by a ZR-75-1 cell and one or more adjuvants, wherein the glycosylated MUC1 molecules comprise glycosylated PDTR (SEQ ID NO:3) regions recognized by an A76-A/C7 antibody, and are able to generate a stimulatory immune response to MUC1-positive tumor cells in vitro, and wherein the glycosylated MUC1 molecules are obtained by
   a) contacting a cell culture supernatant of ZR-75-1 cells containing a mixture of MUC1 molecules with an A76-A/C7 antibody, wherein the A76-A/C7 antibody binds to the glycosylated MUC1 molecules which have glycosylated PDTR (SEQ ID NO:3) regions and is able to form an immune complex;
   b) isolating the immune complex; and
   c) separating the glycosylated MUC1 molecule from the immune complex.

5. The pharmaceutically acceptable composition of claim 4, wherein the mixture of MUC1 molecules is contacted with an A76-A/C7 antibody affinity chromatography column.

6. The pharmaceutically acceptable composition of claim 1, further comprising one or more co-stimulatory molecules.

7. The pharmaceutically acceptable composition of claim 6, wherein the co-stimulatory molecules is selected from the group consisting of an interleukin, GM-CSF, an interferon, and TNF-alpha.

* * * * *

SEQUENCE LISTING

<160> NUMBER OF SEQ ID NOS: 11

<210> SEQ ID NO 1
<211> LENGTH: 1721
<212> TYPE: DNA
<213> ORGANISM: Homo sapiens

<400> SEQUENCE: 1

```
gaattccctg gctgcttgaa tctgttctgc cccctcccca cccatttcac caccaccatg      60
acaccgggca cccagtctcc tttcttcctg ctgctgctcc tcacagtgct tacagttgtt     120
acaggttctg gtcatgcaag ctctacccca ggtggagaaa aggagacttc ggctacccag     180
agaagttcag tgcccagctc tactgagaag aatgctgtga gtatgaccag cagcgtactc     240
tccagccaca gccccggttc aggctcctcc accactcagg acaggatgt cactctggcc       300 ccggccacgg aaccagcttc aggttcagct gccacctggg acaggatgt cacctcggtc       360
```

-continued

```
ccagtcacca ggccagccct gggctccacc accccgccag cccacgatgt cacctcagcc      420
ccggacaaca agccagcccc gggctccacc gccccccag cccacggtgt cacctcggcc       480
ccggacacca ggccgccccc gggctccacc gccccccag cccacggtgt cacctcggcc       540
ccggacacca ggccgccccc gggctccacc gcgcccgcag cccacggtgt cacctcggcc      600
ccggacacca ggccggcccc gggctccacc gccccccag cccatggtgt cacctcggcc       660
ccggacaaca ggcccgcctt ggcgtccacc gcccctccag tccacaatgt cacctcggcc      720
tcaggctctg catcaggctc agcttctact ctggtgcaca acggcacctc tgccagggct      780
accacaaccc cagccagcaa gagcactcca ttctcaattc ccagccacca ctctgatact      840
cctaccaccc ttgccagcca tagcaccaag actgatgcca gtagcactca ccatagcacg      900
gtacctcctc tcacctcctc caatcacagc acttctcccc agttgtctac tggggtctct      960 ttcttttttcc tgtcttttca catttcaaac ctccagttta attcctctct ggaagatccc    1020
agcaccgact actaccaaga gctgcagaga gacatttctg aaatgttttt gcagatttat     1080
aaacaagggg gttttctggg cctctccaat attaagttca ggccaggatc tgtggtggta     1140
caattgactc tggccttccg agaaggtacc atcaatgtcc acgacgtgga gacacagttc     1200
aatcagtata aaacggaagc agcctctcga tataacctga cgatctcaga cgtcagcgtg     1260
agtgatgtgc catttccttt ctctgcccag tctggggctg gggtgccagg ctggggcatc     1320
gcgctgctgg tgctggtctg tgttctggtt gcgctggcca ttgtctatct cattgccttg     1380
gctgtctgtc agtgccgccg aaagaactac gggcagctgg acatctttcc agcccgggat     1440
acctaccatc ctatgagcga gtaccccacc taccacaccc atgggcgcta tgtgcccct     1500 agcagtaccg atcgtagccc ctatgagaag gtttctgcag gtaatggtgg cagcagcctc     1560
tcttacacaa acccagcagt ggcagccact tctgccaact tgtagggca cgtcgccctc      1620 tgagctgagt ggccagccag tgccattcca ctccactcag ggctctctgg gccagtcctc     1680
ctgggagccc ccaccacaac acttcccagg catggaattc                            1721
```

<210> SEQ ID NO 2
<211> LENGTH: 20
<212> TYPE: PRT
<213> ORGANISM: Homo sapiens

<400> SEQUENCE: 2

His Gly Val Thr Ser Ala Pro Asp Thr Arg Pro Ala Pro Gly Ser Thr
1               5                   10                  15

Ala Pro Pro Ala
            20

<210> SEQ ID NO 3
<211> LENGTH: 4
<212> TYPE: PRT
<213> ORGANISM: Homo sapiens

<400> SEQUENCE: 3

Pro Asp Thr Arg
1

<210> SEQ ID NO 4
<211> LENGTH: 8
<212> TYPE: PRT
<213> ORGANISM: Homo sapiens

<400> SEQUENCE: 4

```
Ala Pro Asp Thr Arg Pro Ala Pro
1               5
```

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Thr(GalNac)

<400> SEQUENCE: 5

```
Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser Ala
            20                  25                  30
```

<210> SEQ ID NO 6
<211> LENGTH: 120
<212> TYPE: PRT
<213> ORGANISM: Homo sapiens
<220> FEATURE:
<221> NAME/KEY: misc_feature
<222> LOCATION: (1)..(120)
<223> OTHER INFORMATION: This sequence may encompass 1 to 6
      "VTSAPDTRPAPGSTAPPAHG" repeating units

<400> SEQUENCE: 6

```
Val Thr Ser Ala Pro Asp Thr Arg Pro Ala Pro Gly Ser Thr Ala Pro
1               5                   10                  15

Pro Ala His Gly Val Thr Ser Ala Pro Asp Thr Arg Pro Ala Pro Gly
            20                  25                  30

Ser Thr Ala Pro Pro Ala His Gly Val Thr Ser Ala Pro Asp Thr Arg
        35                  40                  45

Pro Ala Pro Gly Ser Thr Ala Pro Pro Ala His Gly Val Thr Ser Ala
    50                  55                  60

Pro Asp Thr Arg Pro Ala Pro Gly Ser Thr Ala Pro Pro Ala His Gly
65                  70                  75                  80

Val Thr Ser Ala Pro Asp Thr Arg Pro Ala Pro Gly Ser Thr Ala Pro
                85                  90                  95

Pro Ala His Gly Val Thr Ser Ala Pro Asp Thr Arg Pro Ala Pro Gly
            100                 105                 110

Ser Thr Ala Pro Pro Ala His Gly
        115                 120
```

<210> SEQ ID NO 7
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(105)
<223> OTHER INFORMATION: This sequence may encompass 1 to 5
      "AHGVTSAPDTRPAPGSTAPPA" repeating units
<220> FEATURE:
<221> NAME/KEY: MOD_RES
<222> LOCATION: (10)..(10)
<223> OTHER INFORMATION: Thr(GalNac)

```
<220> FEATURE:
<221> NAME/KEY: MOD_RES
<222> LOCATION: (31)..(31)
<223> OTHER INFORMATION: Thr(GalNac)
<220> FEATURE:
<221> NAME/KEY: MOD_RES
<222> LOCATION: (52)..(52)
<223> OTHER INFORMATION: Thr(GalNac)
<220> FEATURE:
<221> NAME/KEY: MOD_RES
<222> LOCATION: (73)..(73)
<223> OTHER INFORMATION: Thr(GalNac)
<220> FEATURE:
<221> NAME/KEY: MOD_RES
<222> LOCATION: (94)..(94)
<223> OTHER INFORMATION: Thr(GalNac)

<400> SEQUENCE: 7

Ala His Gly Val Thr Ser Ala Pro Asp Thr Arg Pro Ala Pro Gly Ser
1               5                   10                  15

Thr Ala Pro Pro Ala Ala His Gly Val Thr Ser Ala Pro Asp Thr Arg
            20                  25                  30

Pro Ala Pro Gly Ser Thr Ala Pro Pro Ala Ala His Gly Val Thr Ser
        35                  40                  45

Ala Pro Asp Thr Arg Pro Ala Pro Gly Ser Thr Ala Pro Pro Ala Ala
50                  55                  60

His Gly Val Thr Ser Ala Pro Asp Thr Arg Pro Ala Pro Gly Ser Thr
65                  70                  75                  80

Ala Pro Pro Ala Ala His Gly Val Thr Ser Ala Pro Asp Thr Arg Pro
                85                  90                  95

Ala Pro Gly Ser Thr Ala Pro Pro Ala
            100                 105

<210> SEQ ID NO 8
<211> LENGTH: 4
<212> TYPE: PRT
<213> ORGANISM: Homo sapiens

<400> SEQUENCE: 8

Asp Thr Arg Pro
1

<210> SEQ ID NO 9
<211> LENGTH: 9
<212> TYPE: PRT
<213> ORGANISM: Homo sapiens

<400> SEQUENCE: 9

Leu Leu Leu Leu Thr Val Leu Thr Leu
1               5

<210> SEQ ID NO 10
<211> LENGTH: 5
<212> TYPE: PRT
<213> ORGANISM: Homo sapiens

<400> SEQUENCE: 10

Pro Asp Thr Arg Pro
1               5

<210> SEQ ID NO 11
<211> LENGTH: 1721
<212> TYPE: DNA
<213> ORGANISM: Homo sapiens
```

```
<400> SEQUENCE: 11
cttaagggac cgacgaactt agacaagacg ggggaggggt gggtaaagtg gtggtggtac        60
tgtggcccgt gggtcagagg aaagaaggac gacgacgagg agtgtcacga atgtcaacaa       120
tgtccaagac cagtacgttc gagatggggt ccacctcttt tcctctgaag ccgatgggtc       180
tcttcaagtc acgggtcgag atgactcttc ttacgacact catactggtc gtcgcatgag       240
aggtcggtgt cggggccaag tccgaggagg tggtgagtcc ctgtcctaca gtgagaccgg       300
ggccggtgcc ttggtcgaag tccaagtcga cggtggaccc ctgtcctaca gtggagccag       360
ggtcagtggt ccggtcggga cccgaggtgg tggggcggtc gggtgctaca gtggagtcgg       420
ggcctgttgt tcggtcgggg cccgaggtgg cggggggtc gggtgccaca gtggagccgg        480
ggcctgtggt ccggcggggg cccgaggtgg cggggggtc gggtgccaca gtggagccgg        540
ggcctgtggt ccggcggggg cccgaggtgg cgcggcgtc gggtgccaca gtggagccgg        600
ggcctgtggt ccggcggggg cccgaggtgg cggggggtc gggtaccaca gtggagccgg        660
ggcctgttgt ccggcggaa ccgcaggtgg cgggaggtc aggtgttaca gtggagccgg         720
agtccgagac gtagtccgag tcgaagatga gaccacgtgt tgccgtggag acggtcccga       780
tggtgttggg gtcggtcgtt ctcgtgaggt aagagttaag ggtcggtggt gagactatga       840
ggatggtggg aacggtcggt atcgtggttc tgactacggt catcgtgagt ggtatcgtgc       900
catggaggag agtggaggag gttagtgtcg tgaagagggg tcaacagatg acccagaga        960 aagaaaaagg acagaaaagt gtaaagtttg gaggtcaaat taaggagaga ccttctaggg      1020
tcgtggctga tgatggttct cgacgtctct ctgtaaagac tttacaaaaa cgtctaaata     1080
tttgttcccc caaaagaccc ggagaggtta taattcaagt ccggtcctag acaccaccat     1140
gttaactgag accggaaggc tcttccatgg tagttacagg tgctgcacct ctgtgtcaag     1200
ttagtcatat tttgccttcg tcggagagct atattggact gctagagtct gcagtcgcac     1260
tcactacacg gtaaaggaaa gagacgggtc agaccccgac cccacggtcc gaccccgtag     1320
cgcgacgacc acgaccagac acaagaccaa cgcgaccggt aacagataga gtaacggaac     1380
cgacagacag tcacggcggc tttcttgatg cccgtcgacc tgtagaaagg tcgggcccta     1440
tggatggtag gatactcgct catggggtgg atggtgtggg tacccgcgat acacggggga     1500
tcgtcatggc tagcatcggg gatactcttc caaagacgtc cattaccacc gtcgtcggag     1560
agaatgtgtt tgggtcgtca ccgtcggtga agacggttga acatcccgt gcagcgggag      1620 actcgactca ccggtcggtc acggtaaggt gaggtgagtc ccgagagacc cggtcaggag     1680
gaccctcggg ggtggtgttg tgaagggtcc gtaccttaag g                         1721
```